US005554528A

United States Patent [19]

Harrison et al.

[11] Patent Number: 5,554,528

[45] Date of Patent: *Sep. 10, 1996

[54] COMPOSITIONS AND METHODS FOR INHIBITION OF HIV PRODUCTION

[75] Inventors: Gail M. Harrison; Ian H. Maxwell; Tyler J. Curiel; Francoise Maxwell, all of Denver, Colo.

[73] Assignee: Board of Revents of University of Colorado, Boulder, Colo.

[ * ] Notice: The term of this patent shall not extend beyond the expiration date of Pat. No. 5,306,631.

[21] Appl. No.: 147,829

[22] Filed: Nov. 4, 1993

Related U.S. Application Data

[63] Continuation-in-part of Ser. No. 685,601, Apr. 15, 1991, Pat. No. 5,306,631, which is a continuation-in-part of Ser. No. 88,086, Aug. 21, 1987, abandoned.

[51] Int. Cl.[6] .............................. C12N 5/00; C12N 15/00

[52] U.S. Cl. ..................................... 435/240.2; 435/320.1; 435/172.3; 435/69.7; 435/948; 536/23.1; 935/27; 935/32; 935/57; 935/71

[58] Field of Search .............................. 435/320.1, 172.3, 435/948, 240.2, 69.7; 536/23.1; 935/27, 32, 57, 71

[56] References Cited

U.S. PATENT DOCUMENTS 4,867,976 9/1989 Ueda et al. .
5,306,631 4/1994 Harrison et al. ...................... 435/172.3

FOREIGN PATENT DOCUMENTS

WO9007936 7/1990 WIPO .

OTHER PUBLICATIONS

Letter to the Editor: Can Diphtheria Toxin be Used for Gene Therapy of Human Immunodeficiency Virus Infection?, (1992) *Aids Research and Human Retroviruses* 12(vol.8): 1949–1950.

Curiel et al. (1993), "Inhibition of Clinical HIV-1 Isolates with a Retrovirus Encoding an HIV-regulated Diphtheria Toxin A (DTA) Chain Gene," Abstract, UCLA Symposia, (Apr. 12–18, 1993).

Wang et al. (1993), "Optimization of Retroviral Transduction Efficiency into Peripheral Blood Mononuclear Cells", Abstract, UCLA Symposia (Apr. 12–18, 1993).

Harrison et al. (1993), "Effects of Enhancer Mutations on the Expression of Human Immunodeficiency Virus 1-regulated Luciferase and Diphtheria Toxin A Chain Genes in Transfected Cells", Toxicon 1(vol.31):85–90.

Curiel et al. (1992), "Inhibition of Clinical HIV-1 Isolates with a Retrovirus Encoding an HIV-regulated Diphtheria Toxin A Chain Gene", Abstract, Aids Conference (San Diego, Dec. 1992).

Harrison et al. (1992), "Inhibition of HIV-1 Production in Cells Transduced with a Retrovirus Containing an HIV–regulated Diphtheria Toxin A Chain Gene", Abstract, Aids Conference (San Diego, Dec. 1992).

Harrison et al. (1992), "Inhibition of Human Immunodeficiency Virus-1 Production Resulting from Transduction with a Retrovirus Containing an HIV-regulated Diphtheria Toxin A Chain Gene", Human Gene Therapy 3: 461–469.

Harrison et al. (1992), "Inhibition of HIV Production in Cells Containing an Integrated, HIV-regulated Diphtheria Toxin A Chain Gene", Aids Research and Human Retroviruses 1(vol.8): 39–45.

Morgan et al. (1992), "Gene Transfer into Primary Culture PBL can Protect Cells from HIV Infection", J. Cell. Bio. Supplement 16F: 49.

Caruso et al. (1992), "Selective Killing of Booby Trapped Cells Prevents Viral Spread in an HIV-infected Cell Population", Abstract, Int. Conf. Aids, Jul. 19–24, 1992.

Klatzmann, D. (1992), "Booby Trapped Cells: A New Approach for Gene Therapy of HIV Infection", Abstract No. PuA 6088, Int. Conf. Aids, Jul. 19–24, 1992.

Venkatesh et al. (1990), "Selective Induction of Toxicity to Human Cells Expressing Human Immunodeficiency Virus Type I Tat by a Conditionally Cytotoxic Adenovirus Vector", Proc. Natl. Acad. Sci. USA 87: 8746–8750.

Maxwell et al. (1990), "Toxin Gene Regulation by HIV-1 Tat and Rev.", Abstract, J. Cell Biochem. Suppl. O (14 part D): 107.

Breitman et al. (1990), "Genetic Ablation in Transgenic Mice with an Attenuated Diphtheria Toxin A Gene", Mol. Cell. Biol. 2(vol.10): 474–479.

Cochrane et al. (1990), "Specific Interaction of the Human Immunodeficiency Virus Rev Protein with a Structured Region in the Env mRNA", Proc. Natl. Acad. Sci. USA 87: 1198–1202.

Miller et al. (1989), "Improved Retroviral Vectors for Gene Transfer and Expression", BioTechniques 9(vol.7): 980–990.

Maxwell et al. (1989), "A DNA Cassette Containing a Trimerized SV40 Polyadenylation Signal which Efficiently Blocks Spurious Plasmid-Initiated Transcription", BioTechniques 3(vol.7): 276–280.

Garcia et al. (1989), "Human Immunodeficiency Virus Type 1 LTR TATA and TAR Region Sequences Required for Transcriptional Regulation", The EMBO J. 8(3): 765–778.

(List continued on next page.)

*Primary Examiner*—Jasemine C. Chambers
*Attorney, Agent, or Firm*—Greenlee, Winner and Sullivan, P.C.

[57] ABSTRACT

All lines of mammalian origin which have been stably transformed with a chimeric toxin gene expressed under the regulatory control of HIV cis-acting sequences and HIV trans-acting factors are provided by the present invention. HIV infection of a cell of such a transformed cell line results in the death of that cell due to the specific induction of toxin gene expression within the cell. As specifically exemplified, the toxin gene is the diphtheria toxin fragment A gene or a tox176 fragment A chain gene. Also provided by the present invention are recombinant nucleic acid molecules suitable for the stable transformation of a mammalian cell line to produce a transformed cell which will effectively commit suicide in response to HIV infection due to induction of toxin gene expression.

20 Claims, 5 Drawing Sheets

OTHER PUBLICATIONS

Hadzopoulou–Cladaras et al. (1989), "The Rev (trs/art) Protein of Human Immunodeficiency Virus Type 1 Affects Viral mRNA and Protein Expression Via a Cis–Acting Sequence in the env Region", J. Virol. 3(vol.63): 1265–1274.

Harrison et al. (1989), "Toward HIV–Regulated Expression of a Diphtheria Toxin A Gene in Transfected Cells," J. Cell. Biochem. Suppl. O(13 part B): 302.

Baltimore et al. (1988), "Intracellular Immunization", Nature 335: 395–396.

Chaudhary et al. (1988), "Selective Killing of HIV–Infected Cells by Recombinant Human CD4–*Pseudomonas* Exotoxin Hybrid Protein", Nature 335: 369–372.

Rosen et al. (1988), "Intragenic Cis–Acting Art Gene–Responsive Sequences of the Human Immunodeficiency Virus," Proc. Natl. Acad. Sci. 85: 2071–2075.

Felber et al. (1988), "A Quantitative Bioassay for HIV–1 Based on Trans–Activation", Science 239: 184–187.

Harrison et al. (1988), "HTLV II Transactivation of a Diphtheria Toxin Gene in Electroporated RAJI Cells", J. Cell. Biochem. Suppl.O (12 Part E): 178.

Palmiter et al. (1987), "Cell Lineage Albation in Transgenic Mice by Cell–Specific Expression of a Toxin Gene", Cell 50: 435–443.

Nabel and Baltimore (1987), "An Inducible Transcription Factor Activates Expression of Human Immunodeficiency Virus in T Cells", Nature 326: 711–713.

Maxwell et al. (1987), "Cloning, Sequence Determination, and Expression in Transfected Cells of the Coding Sequence for the Tox 176 Attenuated Diphtheria Toxin A Chain", Mol. Cell. Biol. 4(vol.7): 1576–1579.

Maxwell et al. (1987), "HTLV–Regulated Expression of a Transfected Diphtheria Toxin Gene", Abstract J.Cell. Biochem. Suppl. O(II Part D): 67.

Gilboa et al. (1986), "Transfer and Expression of Cloned Genes Using Retroviral Vectors", BioTechniques 6(vol.4): 504–512.

Rosen et al. (1985), "The Location of Cis–Acting Regulatory Sequences in the Human T Cell Lymphotropic Virus Type III (HTLV–III/LAV) Long Term Repeat", Cell 41: 813–823.

Yamaizumi et al. (1978), "One Molecule of Diphtheria Toxin Fragment A Introduced into a Cell Can Kill the Cell", Cell 15: 245–250.

Uchida et al. (1973), "Diphtheria Toxin and Related Proteins", J. Biol. Chem. 11(vol.248): 3838–3844.

LNX-TH43R

LNX-TH43R176

COMPOSITIONS AND METHODS FOR INHIBITION OF HIV PRODUCTION

This work was supported at least in part by funding from the National Institutes of Health. The United States government has certain rights in this invention.

CROSS-REFERENCE TO RELATED APPLICATIONS

This application is a continuation-in-part of U.S. Ser. No. 07/685,601, filed Apr. 15, 1991, now U.S. Pat. No. 5,306, 631 which is incorporated by reference in its entirety herein and which is a continuation-in-part of U.S. Ser. No. 07/088, 086, filed Aug. 21, 1987, now abandoned, which is in its entirety incorporated by reference herein.

FIELD OF THE INVENTION

The present invention provides a novel approach to achieve selective lethality of target cells. This approach involves the selective expression within the target cells of active toxin from chimeric toxin genes. Specifically, a toxin coding sequence is expressed under the regulatory control of HIV cis-acting nucleotide sequences and HIV trans-acting factors.

BACKGROUND OF THE INVENTION

The present invention is based on the surprising discovery that the diphtheria toxin fragment A can be selectively targeted to certain mammalian cell types by introduction into the cell of chimeric toxin genes in which expression of a toxin fragment A coding sequence is controlled by mammalian cell-specific regulatory sequences. The toxin fragment A coding sequence is selectively expressed in the target mammalian cell, inhibiting protein synthesis and resulting in cell death. Cell-specific expression of such chimeric toxin genes was sufficiently restricted to effect selective killing of targeted cells without elimination of nontargeted cells. It was surprising that selective lethality could be obtained using such chimeric toxin genes because there was evidence that the introduction of a single molecule of fragment A into a cell would be lethal (Yamaizumi et al. (1978) Cell 15:245–250) and it was not known, prior to the present invention, if cell-specific regulation would be restricted enough to cause selective lethality.

Attempts have been made to use the diphtheria toxin A fragment to selectively kill undesirable cells, such as malignant cells, without destroying healthy cells. Such attempts have concentrated on replacement of the natural fragment B protein delivery mechanism with alternate delivery mechanisms based on the specificity of certain proteins for cell surface molecules, for example by preparing toxin fragment A protein conjugates with antibodies (immunotoxins), hormones or plant lectins.

In nature diphtheria toxin is synthesized and secreted by strains of *Corynebacterium diphtheria* which are lysogenic for bacteriophage $\beta^{tox+}$. Diphtheria toxin inhibits protein synthesis in and is toxic to most eukaryotic cells that have been tested. The naturally occurring toxin, which is bacteriophage encoded, is a single polypeptide of about 58 kd (535 amino acids). The toxin is composed of two regions, separable by proteolytic cleavage, which are functionally distinct. Toxin activity is associated only with fragment A, the $NH_2$-terminal region of 193 amino acids. Fragment A functions by catalyzing the inactivation of eukaryotic elongation factor-2 (EF-2). The COOH-terminal 342 amino acid fragment B, is itself nontoxic, but functions to deliver the toxin fragment A to cells. Fragment A is nontoxic unless it is introduced into the cell cytoplasm. A review of the structure and function of diphtheria toxin is provided in Pappenheimer (1977) Ann. Rev. Biochem. 46:69–94.

The entire diphtheria toxin gene has been cloned and sequenced by separately cloning fragments having little or no toxic activity (Greenfield et al. (1983) Proc. Natl. Acad. Sci. USA 80:6853–6857). The coding sequence of the mature toxin is preceded by a signal sequence which is believed to function in secretion of tox gene product (Kaczorek et al. (1983) Science 221:855–858). Several nontoxic mutant tox genes have also been cloned including tox45 (Leong et al. (1983) Science 220:515–517) which has a wild-type region A and nonfunctional B region, and tox228 (Kaczorek et al. (1983) supra) which carries mutations in both the A and B regions. Uchida et al. (1973) J. Biol. Chem. 248:3838–3844 and ibid. pp. 3845–3850 have identified several mutant DT proteins, including one with reduced toxicity (CRM176). The attenuated toxicity (about 90% of wild-type) of CRM176 results from a mutation which affects enzymatic activity of the tox176 fragment A.

Specific cellular DNA sequences which function in cell- or tissue-specific regulation have been isolated and identified in many cases. In most mammalian systems studied, cell-specific expression is mediated by an enhancer, a cis-acting DNA sequence, which is believed to selectively activate expression in a target cell in response to tissue or cell-specific trans-acting factors. Examples include immunoglobulin heavy chain (IgH) enhancers which are selectively active in B-cells (Gillies et al. (1983) Cell 33:717–728; Picard and Shaffner (1984) Nature 307:80–82; Ephrussi et al. (1985) Science 227134–140), control elements for elastase cell-specific expression (Hammer et al. (1987) Mol. Cell. Biol. 7:2956–2967), insulin (Edlund et al. (1985) 230:912–916) and interleukin-2 (Fujita et al. (1986)). It has been reported that cell-type specificity of immunoglobulin genes is conferred not only be the IgH enhancer but also by a 5'-upstream element associated with an immunoglobulin gene promoter, which upstream element appears to act independently of the IgH enhancer (Mason et al. (1985) Cell 41:479–487; Foster et al. (1985) Nature 315:423–425). A similar 5'-upstream promoter associated element is reported to function in insulin gene regulation (Edlund et al. (1985) supra), but no such enhancer-independent promoter-associated element has been reported for interleukin-2 regulation (Fujita et al. (1986) supra).

Maxwell et al. (1986) Cancer Research 46:4660–4664 reports the selective killing of B-cells due to expression of an IgH enhancer-regulated diphtheria toxin fragment A gene and suggests that cell-specific regulatory mechanisms can be employed generally for selective cell killing by expression of a toxin gene, with applications in cancer therapy. Maxwell et al. (1987) Mol. Cell. Biol. 7:1576–1579 describes the cloning and sequencing of the attenuated diphtheria toxin 176 and suggests the use of the tox176 coding region for selective cell killing.

Palmiter et al. (1987) Cell 50:435–443 reports that a chimeric diphtheria toxin A coding sequence expressed under the regulatory control of elastase I enhancer/promoter sequences was selectively expressed in pancreatic acinar cells. Selective expression and selective lethality of the chimeric toxin gene was demonstrated by the production of transgenic mice lacking a normal pancreas. Breitman et al. (1987) Science 238:1553–1555 reports that expression of diphtheria toxin fragment A coding sequences under the control of gamma crystallin gene regulatory sequences resulted in selective elimination of lens tissue in transgenic mice.

Proposed treatments for Acquired Immune Deficiency Syndrome (AIDS) include "intracellular immunization" a term coined by Baltimore (1988) Nature 335:7395–7396) to describe the genetic modification of cells to render them incapable of supporting viral production. The present inventors have explored the use of regulated expression of the diphtheria toxin A fragment coding sequences and the attenuated toxin fragment gene tox176 to selectively kill cells infected with human immunodeficiency virus (HIV-1).

As described herein, the present inventors have placed expression of the luciferase (luc) reporter gene, or of diphtheria toxin fragment A coding sequences, under control of the HIV-1 trans-acting, essential Tat and Rev proteins. The Tat protein acts on a cis-acting element mapped to region +14 to +44 (referred to as the TAR region) of the HIV long terminal repeat (LTR) to increase viral expression from the LTR (Arya et al. (1985) Science 229:69–73; Rosen et al. (1985) supra; Sodroski et al. (1985) supra; Green et al. (1989) Cell 58:215–223). The Tat protein appears to exert effects at both transcriptional (Peterlin et al. (1986) Proc. Natl. Acad. Sci. USA 83:9734–9738; Hauber et al. (1987) Proc. Natl. Acad. Sci. USA 84:6364–6368; Laspia et al. (1989) Cell 59:283–292) and post-transcriptional levels (Cullen (1986) Cell 46:973–982; Feinberg et al. (1986) Cell 46:807–817; Wright et al. (1986) Science 234:988–992; Braddock et al. (1989) Cell 58:269–279; Edery et al. (1989) Cell 56:303–312). Tat can stimulate expression of heterologous genes placed 3' to the TAR region (Tong-Starksen et al. (1987) Proc. Natl. Acad. Sci. USA 80:6845–6849; Felber and Pavlaskis (1988) Science 239:184–187). The Rev protein relieves the negative regulatory effect of cis-acting repressive sequences (crs) found in the env region of the HIV-1 genome (Rosen et al. (1988) Proc. Natl. Acad. Sci. USA 85:2071–2075; Hadzopoulou-Cladaras et al. (1989) J. Virol. 63:1265–1274) which repress the production of viral unspliced and singly spliced messenger RNAs (mRNAs). The Rev protein acts by binding to RNA at the Rev responsive element (RRE; Malim et al. (1989) Nature 338:254–257; Cochrane et al. (1990) Proc. Natl. Acad. Sci. USA 87:1198–1202), also localized to the env region; binding of the Rev protein to the RRE is essential for Rev function. Rev protein expression results in an increased accumulation of unspliced and singly spliced viral mRNAs, encoding structural proteins, in the cytoplasm (Felber et al. (1989) Proc. Natl. Acad. Sci. USA 86:1495–1499; Zapp and Green (1989) Cell 58:215–223). Thus, expression of the Rev protein promotes the transition from early to latent infection to productive infection. Like Tat, the Rev protein can also act in trans to activate expression of heterologous genes which contain the negative crs sequences and a correctly oriented RRE (Rosen et al. (1988) supra; Felber et al. (1989) supra). The inventors demonstrate herein that efficient regulation of both chimeric luc and chimeric diphtheria toxin fragment A expression by the Tat and Rev proteins can be achieved in transfected cells in vitro. Such regulation is applicable in the treatment of AIDS, exploiting the extreme toxicity of diphtheria toxin fragment A or of the attenuated tox176 fragment A to kill virus-infected cells.

SUMMARY OF THE INVENTION

It is an object of the present invention to provide cells which have been stably transformed with an HIV-regulated diphtheria toxin A coding sequence expressed under the regulatory control of HIV cis-acting sequences and trans-acting factors, wherein those cells would have been infectible with HIV but for the transformation. By virtue of the tightly regulated diphtheria toxin fragment A coding sequences, when any of these cells are infected with HIV, selective killing of the HIV-infected cells results from HIV-regulated induction of the chimeric such that the HIV cannot be replicated and propagated to additional cells. The selective killing of HIV-infected cells results from the HIV-regulated expression of the cytotoxic toxin (e.g., diphtheria toxin A fragment) protein gene in response to trans-acting regulatory factors produced during HIV replication. As embodied herein, HIV-infected cells are targeted for selective killing using a recombinant diphtheria toxin A chain gene expressed under the regulatory control of HIV cis-acting sequences from the env region responsive to the Rev protein placed downstream of the toxin coding sequence and sequences from the LTR region responsive to the Tat protein placed upstream of the toxin coding sequence to produce an HIV-regulated chimeric toxin gene. Expression of the chimeric toxin gene is activated by the Tat and Rev proteins of HIV. In particular embodiments of plasmid-carried HIV-regulated toxin sequences, the upstream cis-acting regulatory sequences are those of nucleotides −167 to +80 of HIV LTR, and the downstream regulatory sequences comprise the crs sequences and the Rev response element (RRE) in the region of nucleotides 5925 to 8608 region of the HIV-1 env gene. In the alternative embodiments of retrovirus-carried HIV-regulated toxin sequences, the Rev response element is contained within the 5925 to 8490 region of the env gene. The toxin coding sequence is that of the A chain of diphtheria toxin. The encoded diphtheria toxin A chain can be of wild-type activity or attenuated in activity. In a second embodiment a host is protected from HIV infection by the stable transformation of an HIV-regulated toxin gene in target cells which can be infected with HIV. When a stably transformed target cell becomes infected with HIV, then the expression of the toxin gene is induced by the viral Tat and Rev proteins, and the death of that cell results from the lethal intracellular action of the toxin A chain. Cell death will occur before the virus can proliferate, and infection of further cells will be prevented because there will be no progeny virus released. The selectivity in killing target cells entails minimal killing, preferably no killing, of nontarget cells; as specifically exemplified, target cells are infected with HIV and nontarget cells are not infected with HIV.

As provided herein, an HIV-regulated diphtheria toxin A gene can be stably introduced into an HIV-infectible cell using a number of art-known vectors, preferably a recombinant retrovirus vector which contains the chimeric toxin gene capable of selective expression only in the presence of HIV trans-acting factors.

Any means known to the art can be used to stably transform target host cells. For example, liposomes containing recombinant DNA molecules and specific for HIV-infectible cells or HIV-infectible cell-specific recombinant retroviruses containing the HIV-regulated toxin gene can be used to introduce the chimeric toxin gene into host cells. Liposomes are especially useful in the genetic engineering of Bone Marrow cells, particularly CD34+ cells, to contain HIV-regulated toxin sequences. Where it is desired to kill cells already infected with HIV, there is no need for stable transfection of the host cells. Where it is desired to protect HIV-infectible cells from HIV infection, it is necessary that the cells be stably transfected with the chimeric toxin gene without killing uninfected cells. For this application, it may be desirable to use a diphtheria toxin fragment A gene which encodes an attenuated toxin A chain to minimize cell death in the absence of inducing HIV. A preferred embodiment of an attenuated diphtheria toxin fragment A gene is the tox176 sequence. Another preferred embodiment is one in which the regulation of the HIV-regulated chimeric toxin gene is sufficiently tightly down-regulated in the absence of HIV trans-acting factors that lethal amounts of the toxin are not produced. The skilled artisan knows how to select the appropriate toxin coding sequence, the appropriate recombinant nucleic acid molecule and the means to introduce it according to the intended use.

Another aspect of the present invention is the use of the combination of recombinant DNA molecules comprising HIV-regulated luciferase and HIV-regulated diphtheria A chain genes in the assay of potentially therapeutic compositions for use in the treatment of AIDS. The dependence of luciferase expression on HIV trans-acting functions and the diphtheria toxin fragment A-mediated inhibition of luciferase allows the assessment of viral replication as a function of a decrease in luciferase activity. The measurement of protein synthesis in general by any means known to the art will allow the determination that the decrease in protein synthesis is due to diphtheria toxin fragment A gene expression rather than to a failure to induce the expression of the luciferase gene. It is further understood that an HIV-regulated luciferase gene can be used in an assay for HIV infection or for the presence of Tat and Rev proteins, with the measurement of luciferase activity or with transcriptional expression of the luciferase coding sequence. The use of either a stably transfected cell line or a transient expression assay will serve for these purposes.

BRIEF DESCRIPTION OF THE FIGURES

FIG. 2, Panel A, gives the basal expression of PTHA41 and PTHA43 in HeLa, Jurkat, 3T3 and EL-4 cells. Cells were co-transfected with 4 μg of luc reporter (pRSVL) and 0.2 μg of either PTHA42, PTHA41, PTHA44 or PTHA43. Cells were harvested for assays 16 hours following electroporation. Luciferase levels are expressed as a percentage of control: for LUC+PTHA41, the control was LUC+PTHA42; for LUC+PTHA43, the control was LUC+PTHA44. Solid bars, HeLa; diagonally hatched bars, Jurkat; stippled bars, 3T3; horizontally striped bars, EL4. Data with HeLa and Jurkat cells were from two experiments each, performed with duplicate samples. Data with 3T3 and EL4 cells were from one experiment each, performed with duplicate samples.

In FIG. 2, Panel B, which shows trans-activated expression, HeLa cells were co-transfected with 4 μg of PRSVL, and 0.2–0.3 μg of PTHA43 or PTHA44 with or without 1.0–1.5 μg each of pH3tat and/or pH3art (with PTHA42 filler added to a total of either 6.2 or 7.3 μg), and harvested for assays 15–16 hours following electroporation. Luciferase levels are expressed as a percentage of the corresponding control (that obtained with PRSVL+filler PTHA44+the corresponding amounts of the other plasmids). Expression of the results in this way corrected for a slight inhibitory effect of pH3tat on PRSVL expression. Each bar represents an average from four experiments, performed with duplicate samples. Standard deviations are indicated by the error bars.

In FIG. 3, Panel A, lanes are: 1, 43-A2; 2, 43-B4; 3, 43-C2G; 4, 43-A5; 5, 43-D6; 6, 43-D4; 7, 43-C3; 8, 43-C21; 9, reagents only.

In FIG. 3, Panel B, lanes are: 1–4, 43-C21; 5–8, 43-C3; 9–12, 43-D4. Cells were either not transfected (lanes 1,5,9); or transfected with 2.5 μg pLUCA43 (2,6,10) or 2.5 μg each of pLUCA43+pH3tat+pH3art (3,4,7,8,11,12). RNA was reverse transcribed for all lanes except 4, 8 and 12, which were mock reverse transcribed with no reverse transcriptase added. The band in lane 10 was only faintly visible.

DETAILED DESCRIPTION OF THE INVENTION

Figure 1:
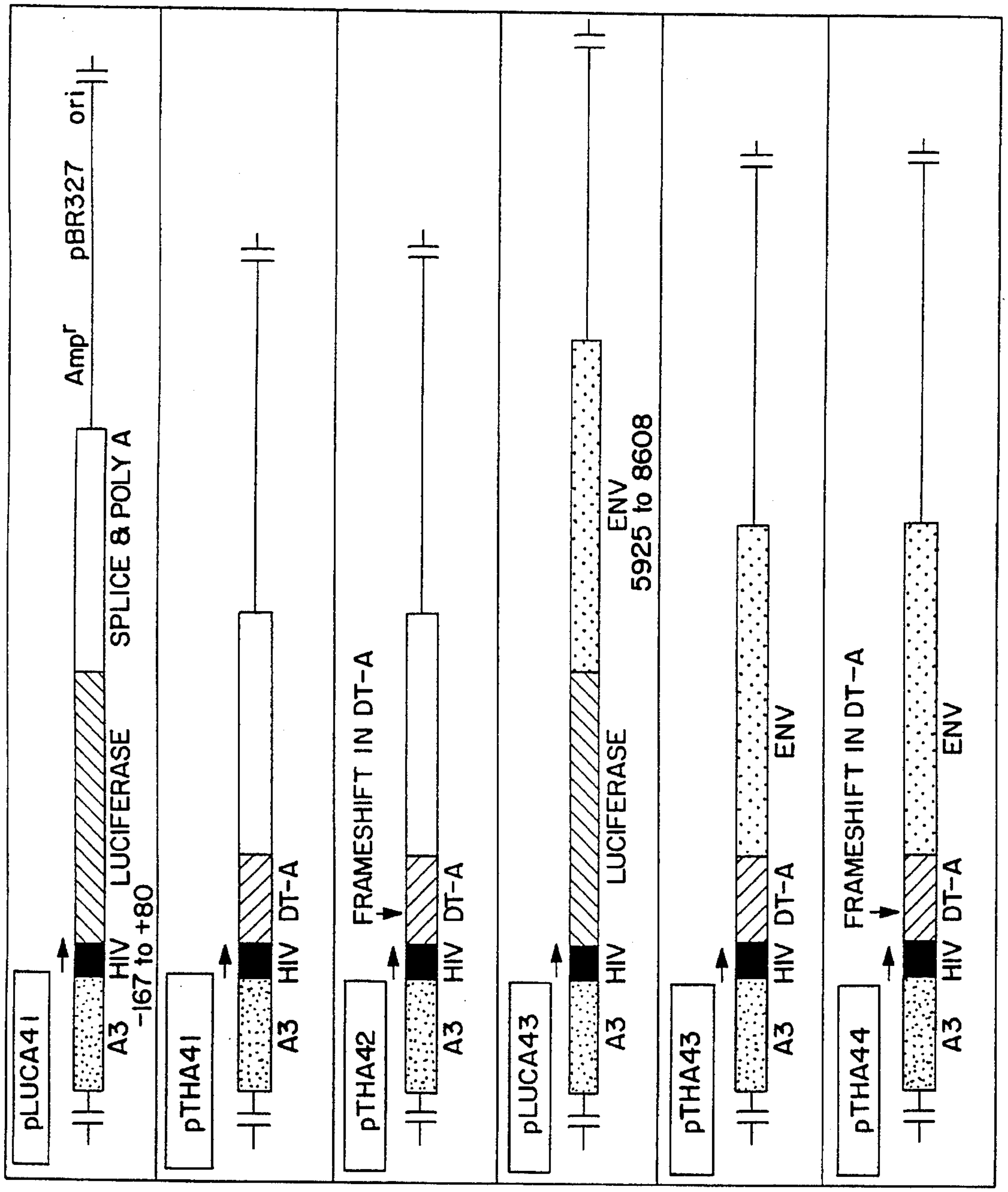
FIG. 1 illustrates the HIV LTR-driven luciferase and diphtheria toxin fragment A expression plasmids used in transient expression assays. The HIV-1 LTR from nucleotide −167 to +80 is present; this includes the enhancer and the Tat-responsive element (TAR). The luc gene was derived from plasmid pSV2A-LUC (de Wet et al. (1987), and the diphtheria toxin fragment A gene from pTH7 (Maxwell et al. (1989) Biotechniques 7:276–280). SV40 sequences in pLUCA41, pTHA41 and pTHA42 include the small t intron and the polyadenylation signal. pBR327 sequences include the origin of replication (ori) and the gene conferring ampicillin resistance (amp). The A trimer is a trimerized version of the SV40 polyadenylation signal previously described (Maxwell et al. (1989) supra). The env region in pLUCA43, pTHA43 and pTHA44 contains nucleotides 5925–8608 from the HIV-1 genome and includes sequences which decrease basal expression (crs) and sequences which confer Rev-responsiveness (RRE).

The term "intracellular immunization" refers to the genetic modification of cells to render them incapable of supporting productive virus infection (Baltimore (1988) supra). One example of this approach was the stable transformation of a mutant HIV gag gene into cells; these cells could not support HIV production (Trono et al. (1989) Cell 59:112–120).

Tightly regulated diphtheria toxin fragment A is ideally suited for use in intracellular immunization, due to its rapid action and its potency. Compared with other gene therapy approaches, which generally require sustained expression of substantial amounts of protein, the regulated diphtheria toxin fragment A approach requires only transient expression of relatively small amounts of protein for killing an HIV-infected cell. Furthermore, when controlled by the early viral regulatory proteins, regulated diphtheria toxin fragment A gene expression should result in cell death before viral production and release begin (about 24 hours after infection, as measured in a model system using H9 cells (Kim et al. (1989) J. Virol. 63:3708–3713)). Because the methods of the present invention mediate the killing of an HIV-infected cell and substantially prevent the release of progeny virus, the spread of infection within a patient is prevented. Thus, if the person has been treated before infection, establishment of infection will be prevented, or if an infected person is treated before the onset of clinical AIDS symptoms, then disease symptoms should be substantially prevented.

As used herein, a toxin gene encodes a cytotoxic protein active in target cells. In the present case the toxin gene is specifically exemplified by a diphtheria toxin fragment A coding sequence, which differs somewhat from the wild-type DT-A coding sequence (see Example 1). This variant DT-A sequence appears to be fully active, and, thus, functionally equivalent to the wild-type diphtheria toxin fragment A sequence. The term "toxin gene" also encompasses toxin fragment A coding sequences with attenuated activity as compared with the wild-type diphtheria toxin fragment A, e.g. the tox176 attenuated coding sequence. The skilled artisan will understand that a wild-type diphtheria toxin fragment A coding sequence can be used in the present invention, and that other toxin genes, which have similar rapid action on cellular processes leading to viral reproduction, can be substituted for the diphtheria toxin fragment A genes of the present invention.

An HIV-regulated chimeric toxin gene of the present invention is selectively expressed in the presence of the HIV Tat and Rev proteins. HIV regulatory control is provided by HIV LTR sequences placed upstream of the toxin coding sequence and by HIV-1 env sequences comprising the crs sequence and RRE placed downstream of the toxin coding sequence. In the HIV-regulated chimeric toxin gene basal expression (in the absence of Tat and Rev) must be sufficiently low so that cell death does not occur. Lethal amounts of toxin are synthesized when the cell containing the HIV-regulated chimeric toxin gene is infected with HIV and Tat and Rev are produced (or when expressible HIV Tat and Rev protein genes are introduced).

An HIV-regulated chimeric luciferase gene of the present invention encodes enzymatically active luciferase, and is regulated in the same manner as the HIV-regulated chimeric toxin gene described above.

As used herein, the term "selective killing" refers to killing of a target cell but not a nontarget cell, even if both types of cells are present in a mixture, as in cell culture or if both types of cells are present in a human patient, and is mediated by an HIV-regulated chimeric toxin gene. In the context of the present application, a target cell is one which has been infected with HIV or one which becomes infected with HIV. A nontarget cell as used herein is a cell which is not or cannot be infected with HIV. More generally within the present context, target cells contain the HIV Tat and Rev proteins which will activate the lethal synthesis of an HIV-regulated chimeric toxin gene. The natural functions of the nontarget cell should not be significantly affected by the presence of an HIV-regulated chimeric toxin gene.

The "HIV trans-acting factors" of the present invention are those soluble proteins which mediate regulation of gene expression by interacting with HIV cis-acting regulatory sequences. As specifically exemplified herein, the HIV Tat and Rev proteins interact with the TAR and RRE cis-acting sequence elements so as to activate the expression of the associated coding sequence. The art understands that there will be differences among HIV strains and that there will be variations in regulatory protein sequences and cis-acting regulatory sequences, which do not result in a change in function. It is also understood that the skilled artisan can make modifications to naturally occurring amino acid or nucleotide sequences without significantly affecting function; the art knows how to test modified or naturally occurring variant sequences and proteins for maintenance of function. All naturally occurring and manmade variant sequences of HIV regulatory sequences and factors which mediate selective gene expression as described herein are encompassed by the description and claims. Selective gene expression requires that basal expression (in the absence of HIV trans-acting factors) be sufficiently low so as not to be lethal and that expression of an HIV-regulated toxin coding sequence in the presence of HIV trans-acting factors in a cell be sufficiently high to allow for killing of that cell.

An "HIV-infectible cell," as used herein, is a cell which is capable of being infected by HIV. Generally, HIV-infectible cells are recognized by the presence of the CD4 surface glycoprotein, which serves as the receptor for HIV in human T4 cells (see, e.g., Maddon et al. (1985) Cell 42:93–104).

The "HIV cis-acting regulatory sequences" of the present invention are those which confer regulatable gene expression to a coding sequence associated with them. The HIV cis-acting regulatory sequences of the present invention include the TAR element, which mediates activation of downstream genes in the presence of the HIV Tat protein, the RRE which down-regulates expression of associated gene expression in the absence of the Rev protein, and the crs sequence, which also down-regulates associated gene expression. Preferably, the HIV cis-acting regulatory sequences will be placed in orientations, distances and positions relative to the regulated gene which are similar to natural positions, distances and orientations relative to natural regulated genes. The HIV TAR, RRE and crs sequences are known to the art.

It is further understood that the art may discover other regulatory sequences and activating factors to be added to an HIV-regulated chimeric toxin gene, which can further increase selectivity of associated gene expression. The skilled artisan can also add additional known regulatory sequence elements to mediate inducible gene expression, such as a regulatory sequence responding to an environmental signal such as heat, cold or a chemical compound.

As used herein, "stable transformation" of an HIV-regulated chimeric toxin gene means that the HIV-regulated chimeric toxin gene is maintained in the cell into which it has been introduced for a sufficient time to mediate lethal synthesis of the toxin gene if and when HIV infection of that cell should occur, and maintenance of the chimeric gene will be such that HIV-dependent regulation remains intact. Basal expression will be sufficiently low (or absent) so that toxin gene-dependent killing of the cell will not occur in the absence of the HIV Tat and Rev proteins.

A "recombinant DNA molecule," as used herein is one in which portions of different origins are covalently linked, and wherein the recombinant DNA molecule replicates in suitable host cells. Generally, one portion will comprise vector sequences; the vector sequences can be plasmid or retroviral, among others. In the present invention, HIV-regulated chimeric toxin genes are linked to vector sequences, thus, allowing amplification of the DNA molecule and providing a suitable vehicle for introducing the chimeric toxin genes into host cells, e.g., HIV-infectible cells. Portions of the recombinant DNA molecule can be from natural sources, from sources propagated in culture, or they may be prepared by chemical synthesis. The portions are typically joined by molecular biological techniques, for example, using DNA ligase. Joining of nucleic acid portions from different sources may also be accomplished by taking advantage of homologous recombination mechanisms within a host cell, e.g., when two different molecules, each containing a region homologous to the other are introduced into that host cell. In sum, recombinant DNA molecules of the present invention are produced by or directed by the hand of man.

In developing the targeted expression of diphtheria toxin fragment A coding sequences as a gene therapy approach to AIDS, it is important to minimize (or eradicate) leaky toxin gene expression. Further reduction of basal expression of diphtheria toxin fragment A coding may be obtainable by utilizing mutations in the promoter region (Nabel and Baltimore (1987) Nature 326:711–713) or less active mutants of diphtheria toxin fragment A coding sequences (Maxwell et al. (1987) supra; Breitman et al. (1990) Mol. Cell Biol. 10:474–479). The chimeric toxin genes of the present invention show significant selectivity for killing target cells, but not nontarget cells. The HIV genome provides other regulatory systems (reviewed in Jones et al. (1988) Genes & Devel. 2:1101–1114; Garcia et al. (1989) EMBO J. 8:765–778) which could be exploited to increase the specificity of expression and trans-activation level of a toxin gene. Ultimately, the applicability of regulated diphtheria toxin fragment A gene expression in therapy will depend not only on obtaining very stringent HIV-dependent regulation (as has been achieved in vitro utilizing tissue-specific promoters in transgenic mice, (Breitman et al. (1987) supra; Palmiter et al. (1987) supra), but also on the availability of a gene therapy protocol to introduce the diphtheria toxin fragment A construct, e.g., by retroviral transduction (Eglitis and Anderson (1988) BioTechniques 6:608–614; Miller and Rosman (1989) BioTechniques 7:980–984), into a patient's lymphocytes, macrophages, glial and/or marrow stem cells.

The ability to specifically kill HIV-infected cells at an early stage of the viral infection cycle will provide an efficient means of blocking the spread of infectious virus. This can be achieved by the introduction of a gene encoding a lethal product, linked with regulatory elements that respond specifically to viral trans-activating proteins. For this purpose the gene encoding the A fragment of diphtheria toxin, which potently inhibits protein synthesis by enzymatically inactivating elongation factor 2 can be used. The use of the poliovirus 2A protein as an alternative lethal product has also been suggested (Sun and Baltimore (1989) supra).

The diphtheria toxin fragment A gene has been shown capable of ablating specific cell populations in mice, demonstrating the feasibility of imposing stringent regulation in vivo on the expression of a potent toxin. The tat and rev genes of HIV, both essential for productive infection, encode trans-acting proteins which strongly enhance the cytoplasmic accumulation of viral mRNAs (Malim et al. (1989) supra; Cochrane et al. (1990) supra). Both products are required for the abundant accumulation of the unspliced and singly spliced mRNAs that encode viral structural proteins, and expression of Rev may be viewed as a switch promoting the transition from an early or latent phase of the viral cycle to the late, productive phase (Daefler et al. (1990) Proc. Natl. Acad. Sci. USA 87:4571). As with other heterologous genes (Tong-Starksen et al. (1987) supra; Felber and Pavlakis (1987) supra), the present inventors have shown that the diphtheria toxin fragment A gene expression can be placed under control of Tat and Rev. This was done using plasmid pTHA43, in which the diphtheria toxin fragment A coding sequence was placed downstream of the HIV-1 LTR and upstream of a portion of the env region containing negative regulatory sequences (crs) and the Rev response element (RRE) (see FIG. 1). As reported herein, this regulation is maintained when the pTHA43 transcription unit is stably transformed. Furthermore, such transformants are substantially impaired in the ability to generate virus from a transfected HIV-1 proviral clone.

Both luciferase and diphtheria toxin fragment A expression can be regulated by the HIV-1 trans-acting proteins Tat and Rev in transient transfection experiments, as described herein, for example, with plasmids pLUCA43 and pTHA43, in which luciferase or diphtheria toxin fragment A coding sequences were placed downstream and under the regulatory control of the HIV LTR. Basal expression from these constructs was dramatically reduced (50-fold, for pLUCA43) by the inclusion of negative regulatory (crs) sequences and the Rev response element (RRE) from the HIV genome in the 3' untranslated regions. Additionally, relative trans-activation was increased by the inclusion of these sequences. Both Tat and Rev were required for maximal expression, resulting in 85-fold trans-activation for pLUCA43 and, for pTHA43, inhibition of luciferase expression from 5–30% of the control, depending on the co-transfected luc reporter. The use of the NFK-B mutation contained in env sequence comprising nucleotides 5925–8608 gives very low basal expression and allows significant trans-activation.

Several possibilities could explain the relatively greater trans-activation of pLUCA43, as compared to pTHA43, by Tat and Rev. First, expression from the two plasmids was measured directly for pLUCA43, but indirectly for pTHA43 using a transient co-transfection assay (Maxwell et al. (1986) supra). The indirect assay allowed the detection of diphtheria toxin fragment A gene expression in the relatively small percentage of cells which take up DNA in transfection experiments. Due to the high cellular lethality of diphtheria toxin fragment A, levels of the toxin fragment in transfected cells are very low and is therefore difficult to measure directly. Experiments using the polymerase chain reaction (PCR) should provide a sensitive, quantitative method to directly measure diphtheria toxin fragment A gene transcriptional expression in transfected cells. Secondly, the HIV-regulated gene itself appeared to influence both basal expression and relative trans-activation, as significant differences in these parameters were noted in a comparison of HIV-regulated luciferase, diphtheria toxin fragment A and CAT expression.

HeLa cells with stably integrated pLUCA43 (individual cell lines or pooled clones) showed similar trans-activation of luciferase expression to that observed in the transient transfection assays. Thus, low basal expression and high relative trans-activation levels were maintained upon integration of the HIV-regulated construct. Analogous cell lines stably integrated with pTHA43 have been generated; such cell lines are impaired for HIV production, as demonstrated herein. This demonstration is an important step in the development of toxin gene therapy for AIDS.

In alternative approaches to targeting gene expression to HIV-infected cells, genes encoding poliovirus 2A protein (Sun and Baltimore (1989) Proc. Natl. Acad. Sci. USA 86:2143–2146) or L2-interferon (Bednarik et al. (1989) Proc. Natl. Acad. Sci. USA 86:4958–4962) have been placed under control of the HIV LTR. Both these constructs were activated by Tat in isolated stable cell lines. However, these studies did not appear to incorporate the additional control of the Rev protein as described herein. HIV-regulated expression of a herpes thymidine kinase gene from an adenovirus vector has been proposed as a means of targeting drug-dependent toxicity to HIV-infected cells (e.g., Venkatesh et al. (1990) Proc. Natl. Acad. Sci. USA 87:8746–8750). Venkatesh et al. reported limited success with Rev control, possibly because of the use of more limited sequences from the env region than those employed herein. Other investigators have described the targeting of protein toxins to HIV-infected cells via CD4 (Chaudhary et al. (1988) Nature 335:369–379; Till et al. (1988) Proc. Natl. Acad. Sci. USA 86:1987–1991) or anti-gp41 antibodies (Till et al. (1989) supra) which bind the HIV envelope protein expressed on the surfaces of infected cells. Targeting entry of a chimeric toxin gene to particular cell types, such as in liposome-mediated delivery (reviewed in Kirsch et al. (1987) Ann. NY Acad. Sci. 507:141–154), could be used in conjunction with specifically regulated expression to increase the selectivity of cell killing. WO 90/07936 and WO 90/10015, also present strategies for delivering toxic effector genes and toxin moieties to HIV-infected cells.

The construction of a retrovirus vector to deliver the HIV-regulated diphtheria toxin fragment A gene (or an attenuated derivative such as tox176) provides an additional means for stable integration in cell lines for in vitro studies and ultimately the means for introduction and stable integration of a HIV-regulated toxin gene of the present invention in a human for AIDS prophylaxis or therapy.

In the present study, individual clones of HeLa cells with integrated pTHA43 generate 50–96% less secreted p24 antigen than control cells following transfection with an HIV provirus (Table 1). Although the extent of this decrease varied among clones, for a given clone, greater inhibition of HIV p24 production occurred when the cells were transfected with less proviral DNA (2 μg versus 5 μg). Because of the large number of viral genomes entering a cell by DNA transfection, such experiments may underestimate the efficiency with which the production of viral structural proteins would be inhibited in a genuine infection. The HIV-regulated toxin gene of LNX-TH43R has been introduced into HIV-susceptible, CD4-positive cells, the ability of this construct to inhibit the replication of HIV introduced by infection has been demonstrated.

Use of PCR allowed the detection of the diphtheria toxin fragment A sequence in total cytoplasmic RNA in the HeLa (pTHA43) transformants, even in the absence of induction by transformation with Tat and Rev expression plasmids. The explanation for this observation is at present unclear. It is possible that the cells are able to tolerate a minimal basal level of diphtheria toxin fragment A gene expression, which is detectable only due to the extremely high sensitivity of the PCR. Alternatively, cells within clonal populations might spontaneously express the integrated chimeric diphtheria toxin fragment A sequences at low frequency, presumably with lethal consequences for these cells. This possibility is consistent with the observation of the tendency for cell lines to show increased ability to show pLUCA43 trans-activation as the number of passages in culture increased. Integration of constructs such as pTHA43 or analogous recombinant retroviruses can be maintained, without expression, for long enough periods to be therapeutically useful, e.g., following transduction of bone marrow cells and autologous reimplantation. The skilled artisan will recognize what, if any, modifications in the chimeric genes or vectors are required. For example, if such instability presents a serious problem due to basal toxin expression, the use of an attenuated diphtheria toxin fragment A mutant such as tox176 instead of the wild-type should improve stability by allowing minimal basal expression to be tolerated. Similarly, modifications of cis-acting regulatory sequences can be made to decrease basal expression, and thus improve selectivity of killing and genetic stability, as understood in the art.

In general, the greater the selectivity for killing HIV-infected but not uninfected cells, the more desirable the HIV-regulated chimeric toxin gene. However, it is understood that the particular application for such an HIV-regulated chimeric toxin gene will determine the requisite levels of selectivity and/or basal expression.

Deployment of an HIV-regulated toxin gene for AIDS therapy, like all currently gene therapy approaches, requires an efficient means of introducing the regulated gene construct into substantial numbers of target cells. Retroviral vectors provide an the means for efficient delivery to target cells (Gilboa et al. (1986) BioTechniques 4:504; Miller, A.D. (1990) Blood 76:22)). Retroviral vectors are also described in WO 90/07936, which is incorporated by reference herein. Recombinant retroviruses can be constructed to contain the transcription unit from pTHA43 or of other HIV-regulated diphtheria toxin fragment A coding sequences. Successful production of such vectors without toxicity to the packaging cells, as achieved by the present inventors, provides additional assurance that basal expression has been reduced to tolerable levels.

Intracellular immunization as proposed by Baltimore (1988) supra, involved use of gene transfer to render cells refractory to a viral infection, without toxicity to the cells. Implicit in this concept is the necessity for sustained expression of a product inhibitory to viral replication, probably over an extended period. Substantial expression levels would also be required for certain of the proposed HIV inhibitors, such as dominant negative mutants of gag (Trono et al. (1989) supra) or "TAR decoys" (Sullenger et al. (1990) Cell 63:601), possibly associated with detrimental effects on the cells. In contrast, low level, transient activation of the diphtheria toxin fragment A gene suffices to rapidly kill any cell initiating the HIV infectious cycle, without permitting the generation of viral progeny. Continuous cell replacement occurs with further HIV-refractory cells derived from the genetically modified (i.e., stably transformed) stem cell population containing the regulated toxin gene. Eventually, viral clearance is achieved through the lack of a reservoir of infectible cells capable of replicating the virus.

For AIDS treatment or for prevention of the disease state in an HIV-infected individual, diphtheria toxin fragment A (or attenuated derivatives such as tox176) genes whose expression is tightly regulated by HIV cis-acting sequences and trans-acting factors can be introduced into target cells by any means known to the art. Such constructs can be introduced using recombinant retroviruses, e.g., according to WO 90/07936, or using recombinant DNA molecules introduced via liposome technology, e.g., as described in U.S. Pat. No. 4,867,976. For prophylaxis in an uninfected individual, for example, an individual at high risk due to employment, sexual conduct or medical condition, tightly regulated toxin gene derivatives or recombinant molecules can be introduced into target cells, i.e., those which permit HIV infection, e.g., by incorporation of the recombinant DNA molecules in liposomes targeted to CD4-positive cells by incorporation of CD4-specific antibody, as understood in the art, such that the HIV-regulated toxin gene becomes stably integrated into the genomes of the target cells.

The sensitivity for the detection of the HIV-regulated luciferase expression and its inhibition by HIV-regulated diphtheria toxin fragment A allows the testing of potential therapeutic compositions for their abilities to depress or prevent HIV replication in vitro. If HIV replication, and therefore, expression of the positive regulators Tat and Rev, is depressed, then there is a lower activation of both luciferase and diphtheria toxin fragment A in cells containing both as HIV-regulated genes. Protein synthesis is not inhibited in cells not expressing diphtheria toxin fragment A coding sequences, so appropriate manipulation of incubation time after HIV infection and prior to assay for luciferase activity allows the skilled artisan to distinguish failure to induce from killing by diphtheria toxin fragment A. For safety, serially-noninfectious mutants of HIV, known to the art, are preferably used in such assays. Alternatively the skilled artisan can monitor whether protein synthesis was inhibited, e.g., measuring incorporation of radioactive amino acid(s) into protein (as TCA-insoluble material). The skilled artisan also understands that Tat and Rev proteins can be detected in a cell also bearing an HIV-regulated luciferase gene via an increase in luciferase activity.

An assay of this nature can also be adapted for diagnostic purposes. HIV-infected cells stably transformed with an HIV-regulated luciferase gene as described herein are induced to produce luciferase (and light under appropriate assay conditions) if infected with HIV, e.g., from a biological sample (such as blood containing HIV). It will be understood by the skilled artisan how to modify the assay parameters to generate a valid assay method.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning,* Second Edition, Cold Spring Harbor Laboratory, Plainview, N.Y.; Maniatis et al. (1982) *Molecular Cloning,* Cold Spring Harbor Laboratory, Plainview, N.Y.; Wu (ed.) (1993) Meth. Enzymol. 218, Part I; Wu (ed.) (1979) Meth Enzymol. 68; Wu et al. (eds.) (1983) Meth. Enzymol. 100 and 101; Grossman and Moldave (eds.) Meth. Enzymol. 65; Miller (ed.) (1972) *Experiments in Molecular Genetics,* Cold spring Harbor Laboratory, Cold Spring Harbor, N.Y., Old Primrose (1981) *Principles of Gene Manipulation,* University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization,* IRL Press, Oxford, UK; Setlow and Hollaender (1979) *Genetic Engineering: Principles and Methods,* Vols. 1–4, Plenum Press, New York. Abbreviations and nomenclature, where employed, are deemed standard in the field and commonly used in professional journals such as those cited herein.

This invention is illustrated by the following examples, which are not to be construed in any way as imposing limitations on the scope thereof. It is understood that resort can be made to various other embodiments, modifications, alternatives and equivalents of the procedures materials and techniques specifically described which, after reading the description herein, may suggest themselves to those skilled in the art without departing from the spirit of the present invention and/or the scope of the appended claims.

All of the references cited throughout the present Specification are incorporated by reference, in their entirety.

EXAMPLES

Example 1

Plasmid Construction pTHA41, in which the HIV-1 LTR regulatory is just 5' to the diphtheria toxin fragment A sequence (FIG. 1), was constructed by isolating a 247 base pair XhoI-HindIII fragment containing sequences −167 to +80 of the HIV-1 LTR. This fragment includes the Tat-responsive element, TAR, as well as other regulatory sequences (reviewed in Jones et al. (1988) supra; Garcia et al. (1989) supra). The fragment was made blunt-ended by filling in using Klenow DNA polymerase, and it was then ligated into the SmaI site of pTHA7, a previously described promoterless plasmid (Maxwell et al. (1989) supra) derived from our prototype diphtheria toxin fragment A expression plasmid, pTH1 (Maxwell et al. (1986)). The toxin coding sequence of pTH1 and derivatives varied from the wild-type diphtheria toxin fragment A gene by 2 codons at the amino terminus and an additional 24 codons at the carboxy terminus (Errata (Aug. 10, 1990) Cell 62:facing page 608). The modifications to the diphtheria toxin fragment A coding sequence do not appear to interfere with toxin activity. pLUCA41, pTHA42, pLUCA43, pTHA43 and pTHA44 (FIG. 1) were derived from pTHA41. The "A" in this series of plasmids refers to the "A trimer" a trimerized version of the simian virus 40 (SV40) polyadenylation signal which prevents expression of spurious plasmid-initiated transcripts (Maxwell et al. (1989) supra). A diphtheria toxin fragment A frameshift mutant of pTHA41, designated pTHA42, was constructed for use as "filler" DNA to ensure that all electroporation pulses were with the same amount of HIV LTR-containing DNA. pTHA42 was generated from pTHA41 by filling in an AccI site within the toxin gene, about 100 nucleotides from the 5' end. pLUCA41 was constructed by substituting a HindIII/ApaI fragment containing the coding sequence for luciferase (together with downstream processing signals from SV40) from the plasmid pSV2A.L-A.Δ5' for the corresponding diphtheria toxin fragment A-containing sequence in pTHA41. pSV2A.L-A.Δ5' (subsequently designated pSV2A-LUC), was supplied by S. Subramani, as was pRSVL, expressing luciferase under the control of the Rous sarcoma virus LTR (de Wet et al. (1987) Mol. Cell Biol. 7:725–737).

To construct pTHA43 and pLUCA43, a 2683 base pair KpnI fragment, containing nucleotides 5925–8608 of the HIV-1 genome, was isolated from plasmid pIIIAR (Rosen et al. (1988) supra). An intermediate plasmid, pUC18env, was constructed by inserting this sequence into the KpnI site of pUC18. A second intermediate plasmid, pTHA41Dr, was constructed which removed the SV40 small t intron from pTHA41. To generate pTHA41Dr, pIBI30DT-A was first made by inserting a DraI fragment from pTH7 (Maxwell et al. (1989) supra) containing the diphtheria toxin fragment A gene minus SV40 sequences into the polylinker region of pIBI30DT-A as an NcoI-ApaI fragment which was then cloned into pTHA41 to generate pTHA41Dr, lacking both the SV40 small t intron and polyadenylation signal. During the construction of pTHA41Dr, a SalI site from the polylinker region of pIBI30 was inserted just downstream of the diphtheria toxin fragment A coding sequence. A SalI-EcoRI fragment from pUC18env (see above), containing the HIV-1 sequences was then inserted into the 3' untranslated region of SalI+EcoRI digested pTHA41Dr to generate pTHA43. pLUCA43 was derived from pTHA43 by inserting a HindIII+XmaI fragment from pJD207 (de Wet et al. (1987) supra), containing the luc cDNA, into pTHA43 digested with SphI+XmaI. This ligation was performed after blunt ending the HindIII and SphI sites of pJD207 and pTHA43, using Klenow and T4 DNA polymerases, respectively, in the presence of nucleoside triphosphates. Both pLUCA43 and pTHA43 are presumed to use the A trimer for polyadenylation of transcripts. pTHA44, a toxin frameshift mutant of pTHA43, was constructed as described for pTHA42, filling in and re-ligating at the AccI site within the diphtheria toxin fragment A coding sequence. pTHA41 and pTHA43 are predicted to encode fragment A proteins with C-terminal extensions of 24 and 25 amino acids, respectively, beyond the natural terminus of diphtheria toxin fragment A; the first 22 of these amino acids are identical, as are the N-termini, which differ from authentic fragment A by 3 amino acids (Maxwell et al. (1989) in *Gene Transfer and Gene Therapy,* Alan R. Liss, Inc., New York, pp. 189–264). Plasmids pH3tat and pH3art are expression plasmids for HIV-1 proteins Tat and Rev, respectively (Rosen et al. (1988) supra). Both plasmids have the HIV-1 LTR (sequences −167 to +80) as a promoter. HIV-1 sequences are derived from strain HIV-IIIb (Arya et al. (1985) supra; Fisher et al. (1985) Nature 316:262–265).

The expression plasmids for Tat and Rev, pH3tat and pH3art (Rosen et al. (1988) supra), utilize the HIV-1 promoter. The HIV proviral clone, HXBΔBgl, was derived from HXB2 (Sodroski et al. (1985) supra) by deletion of 500 base pairs between two BglII sites in the env region; HXBΔBgl was a gift from Dr. E. Terwilliger.

pLUCA61 contains the −453 to +80 region of the HIV LTR, the luc gene and the 5925 to 8608 region of HIV and the NF-kB promoter mutation. pTHA61 and pTHA61-176 are analogous with the wild-type activity and attenuated tox176 coding sequences in place of the luc reporter gene. pTHA63 contains the −453 to +80 HIV LTR sequences, the diphtheria toxin fragment A coding sequence, the 5925 to 8608 ENV sequences and the NF-kB+TATA promoter mutations. The promoter mutations were isolated as 533 bp XhoI-HindIII fragments from HIV-CAT plasmids (Nabel and Baltimore (1987) Nature 326:711–713; Nabel et al. (1988) Science 239:1299–1302), blunt-ended with Klenow polymerase and inserted into the SmaI site of pUCA1.5 (Maxwell et al. (1989) Biotechniques 7:276–280) creating intermediate plasmids pUCA1.5/kB and pUCA1.5/kB+TATA. pUCA1.5 contains a trimerized version of the SV40 polyadenylation signal (A3 in FIG. 1) which blocks spurious transcription initiation from vector sequences. The A3/kB and A3/kB+TATA promoter mutation-containing fragments were then isolated as HindIII fragments and inserted into the HindIII sites of fragment A-encoding plasmids to generate pTHA61 and pTHA63, respectively. For pTHA61-176 an intermediate plasmids (pIBI30-176) was generated which contained the tox176 coding sequence in the cloning vector pIBI30 (International Biotechnologies Inc., New Haven, Conn.). The tox176 coding sequences were then re-isolated as an NcoI-SalI fragment, and were inserted in place of the wild-type fragment A, into pTHA61 which had been digested with NcoI and SalI. pLUCA61 was constructed by inserting the A3/kB HindIII fragment from pUCAI.5/kB into a partial HindIII digest of pLUCA43 to replace the wild-type HIV LTR fragment with the mutant kB sequences.

Example 2

Transfections by Electroporation and Transient Assays

All cell types were grown in Opti-MEM medium (Gibco, Grand Island, N.Y.) with 3.8% fetal bovine serum in Falcon T-75 flasks, and were harvested and resuspended in Opti-MEM with 10% fetal bovine serum for the electroporation pulse. HeLa cells were grown to about 80% confluence and were suspended at 2–4×$10^7$ cell/ml to pulse; Jurkat and EL-4 cells (human and murine T cell lines, respectively) were grown to about 1×$10^6$ cells/ml and were suspended at 0.5–1×$10^8$ cells/ml to pulse; H9 cells were grown to 6 to 9×$10^5$ cells/ml and were suspended at about 3–4×$10^7$ cells/ml for pulsing, and 3T3 cells were grown to about 80% confluence and were suspended at 5×$10^6$ cells/ml to pulse.

Cells were transfected using a BioRad Gene Pulser with capacitance extender as previously described (Maxwell and Maxwell (1988) DNA 7:557–562). Pulses were performed in 0.1 ml volumes in Biorad cuvettes with the amounts of DNA indicated. Gene Pulser settings were 220 volts (for HeLa), 250 volts (for Jurkat), 280 volts (for 3T3) or 290 volts (for EL-4), with a capacitance of 250 μfarad, yielding time constants of 25–30 msec. Transient expression of luciferase was measured in lysates prepared 11–21 hours after the pulse. Diphtheria toxin fragment A activity was measured indirectly by its inhibition, presumably at the translational level, of luciferase expression from co-transfected pSV2A-LUC or pLUCA43. Cell harvests, luciferase assays and Biorad protein assays were performed as described (Maxwell and Maxwell (1988) supra), and light units (LUs) measured were corrected to 100 μg of protein. The results are presented in FIG. 3.

The plasmids with mutations in the HIV promoter (pTHA61, pTHA61-176 and pTHA63) exhibited lower basal expression than pTHA43 which contains the wild-type HIV enhancer sequence. pLUCA61 exhibited about 4-fold lower basal expression levels than observed with pLUC43, and the expression was stimulated 96-fold by pH3tat and pH3art. Alterations in the NF-kB binding sites lowered basal expression of both luc and fragment A coding sequences but still allowed trans activation in response to HIV Tat and Rev. However, when mutations in the NF-kB binding sites were combined with either an attenuated diphtheria toxin fragment A gene or mutations in the TATA box of the HIV promoter, trans activation of the diphtheria toxin fragment A gene expression was drastically reduced (See also Harrison et al. (1993) Toxicon 31:85–90, incorporated by reference herein). The NF-kB+TATA mutation does not appear to allow significant trans activation of pTHA63 in the presence of the Tat and Rev proteins.

Example 3

Isolation of Stably Transformed HeLa Cells Expression an HIV-regulated Luciferase Gene Cells were co-transfected by electroporation (as above) with plasmids pLUCA43 and pSV2-327neo, a modified version of the expression plasmid pSV2neo (Southern and Berg (1982) supra). Selection for drug-resistant cells was in 400 μg/ml G418 (Gibco), added fresh every 3–5 days for approximately two weeks. G418-resistant cells were either cloned or maintained as a pooled population, and were assayed for luciferase expression with or without transient transfection of pH3tat and/or pH3art.

HeLa cells were co-transfected by electroporation, using a BioRad Gene Pulser with capacitance extender as previously described (Maxwell and Maxwell (1988) supra), with either plasmids pTHA43 or pTHA44 and pSV2-327neo, a modified version of the expression plasmid pSV2neo (Southern and Berg (1982)supra). Cells were selected in G418 as described above, and were either maintained as pooled populations of about 350 clones (for pTHA43 and pTHA44), or as individual clones in 24-well plates after picking colonies using sterile cotton swabs (for pTHA43 only). The pooled populations, or expanded clones, were assayed for diphtheria toxin fragment A expression using the previously described transient co-transfection assay (Maxwell et al. (1986)supra). Luciferase expression was measured 12–20 hours after transfection of pLUCA43+pH3tat+pH3art (2.0–2.5 μg each). Low luciferase expression could arise by the activation of expression of an integrated diphtheria toxin fragment A gene by Tat and Rev proteins whose synthesis was directed by pH3tat and pH3art. Five of approximately 60 clones assayed exhibited low luciferase expression in the presence of pH3tat and pH3art, and were selected for further analysis.

In some cases, DT antitoxin (Connaught Labs Inc; 62 μg/μl), known to inhibit diphtheria toxin activity, was added to the cell suspension at 4–8% before electroporation.

A further control which demonstrated that the results were due to toxin activity was the experiment carried out in parallel using diphtheria toxin-resistant cells. $2\times10^7$ cells of 43-Da, a HeLa cell line containing pTHA43 sequences was transfected with a 20 μg of DNA of a genomic clone encoding mutant EF-2 (pGHED7-1, from K. Kohno; described in Nakanishi et al. (1988) J. Biol. Chem. 263:6384–6391). After this transfection, diphtheria toxin-resistant cells were selected during growth in 0.5 or 1.0 μg/ml diphtheria toxin. The progeny were examined as pools for luciferase from pLUCA43 in the transient assay system as described herein. Trans-activated luciferase levels were increased over 30-fold in the toxin-resistant cells as compared to the parental 43-Da cell line. Additionally, p24 values were increased 10-fold, as assayed at 2 days following transfection with an HIV provirus. Although the p24 levels were not as high as with the parental HeLa cell line, these data indicate that the expression of the diphtheria toxin fragment A coding sequences were responsible for the lowered luciferase expression and p24 levels in the HeLa cell lines stably transformed with the HIV-regulated chimeric DT-A sequences carried by pTHA43.

Example 4

Figure 2A:
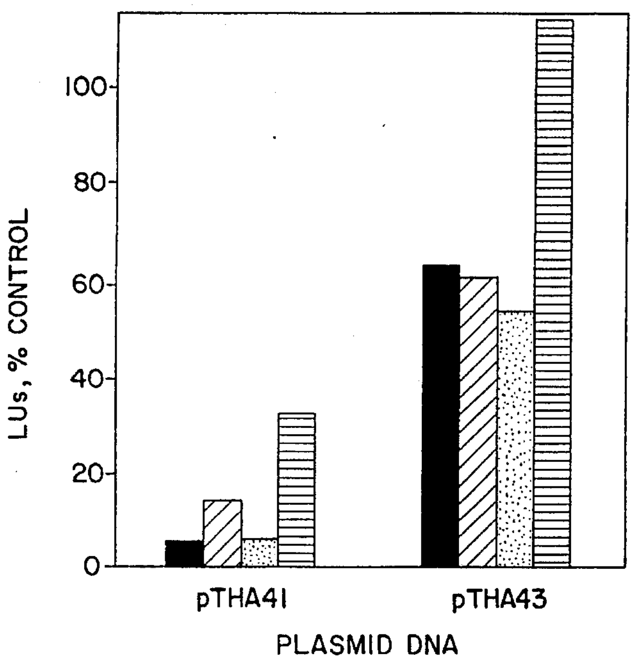
FIGS. 2A–2B illustrates expression of HIV-regulated diphtheria toxin fragment A plasmids in several cell lines.
Figure 2B:
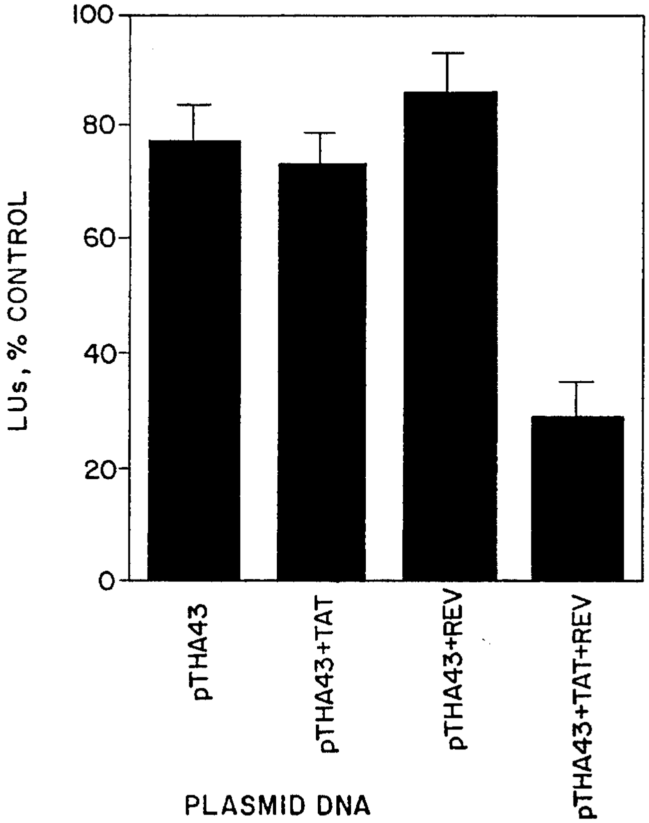

Trans-activation of an HIV-regulated Luciferase Reporter Gene by Tat and Rev Initial experiments aimed at demonstrating trans-activation of an HIV-1 LTR-driven reporter gene used the luc reporter gene described by de Wet et al. (1987) supra. We reasoned that any basal expression of the reporter (that is, expression in the absence of trans-activation) would be easily detected using the highly sensitive luciferase assay. Plasmid pLUCA41 contains the HIV-1 LTR (−167 to +80) 5' to luc cDNA (FIG. 1). This region of the LTR includes the enhancer and the Tat-responsive element, TAR. FIG. 2 shows the basal and trans-activated expression levels from pLUCA41 in HeLa cells, plotted as a ratio of LUs obtained when an equal amount of pSV2A-LUC (expressing luc from the SV40 promoter) was introduced into parallel samples of cells. Expression from pLUCA41 was increased 28-fold in the presence of pH3tat above a basal expression level which was, however, substantial (almost 50% that obtained with pSV2A-LUC). While this level of trans-activation was encouraging, the high basal expression would be unacceptable for HIV-regulated diphtheria toxin fragment A expression, where any (leaky) expression would be potentially lethal to cells.

To decrease basal expression, negative regulatory (crs) sequences from the env region of the HIV-1 genome were incorporated into pLUCA41 to generate pLUCA43. Sequences between nucleotides 6376 and 7760 of the HIV-1 genome strongly inhibit expression of HIV-1 LTR-driven constructs when included in the 3' untranslated region (Rosen et al. (1988) supra), an effect which is overcome by the HIV-1 gene product Rev. pLUCA43 contains nucleotides 5925–8608 of HIV-1 inserted in the 3' untranslated region downstream of the luc coding sequences (FIG. 1). As shown in FIG. 2, this insertion dramatically decreased basal expression from the HIV-1 LTR sequences. Luciferase expression from pLUCA43 in the absence of trans-activation was 1% of that from the pSV2A-LUC control, a reduction of 50-fold compared to pLUCA41. In the presence of pH3tat and pH3art, pLUCA43 expression was increased 85-fold. Thus, the relative level of trans-activation was substantially higher than that of pLUCA41 (85-fold compared to 28-fold). Both Tat and Rev-expressing plasmids were required for maximal expression of pLUCA43; pH3tat alone resulted in only 10-fold activation compared to basal expression, while pH3art, which expresses Rev, alone did not result in detectable activation. pLUCA41 was completely unresponsive to Rev.

In these experiments, pTHA42 (FIG. 1) was used as "filler DNA" so that all electroporations were performed with an equivalent amount of HIV LTR-containing DNA. To rule out the possibility that pTHA42 was inhibiting pLUCA43 expression, perhaps by competing for transcription factors, luciferase expression was measured in HeLa cells electroporated with pLUCA43 with or without pTHA42. In each case, the LUs measured were very low, being only about twice background levels (date not shown). Thus, the low basal expression from pLUCA43 was not attributable to an inhibitory effect of the filler DNA.

Luciferase-expressing stable cell lines were generated by co-transfection of HeLa cells with pLUCA43 and pSV2-327neo, an expression plasmid conferring G418 resistance. G418-resistant cells were either cloned or maintained as a pooled population. Table 2 shows the luciferase activity measured in extracts of these cells with or without transient transfection with the Tat and/or Rev expression plasmids. As in the transient assays, luciferase expression in both the HeLa luc19 clone and the pooled population was weakly activated by pH3tat or pH3art alone, and was strongly activated by pH3tat and pH3art together. This demonstrates that a reporter gene stably integrated into a host genome can be stringently controlled by the HIV regulatory proteins Tat and Rev and crs, and serves as a paradigm for the isolation of analogous cell lines with a stably integrated HIV-regulated diphtheria toxin fragment A gene.

Example 5

Figure 3A:
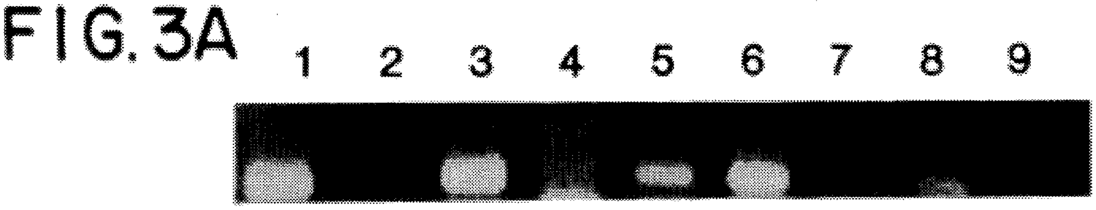
FIGS. 3A–3B shows the results of PCR amplification of a 330 base pair diphtheria toxin fragment A coding sequence from (a) DNA, or (b) RNA (reverse transcribed to cDNA) from pTHA43 positive (43-A2, -C2G, -C21, -D4, -D6) or pTHA43 negative (43-B4, -A5, -C3) clones. Oligonucleotide primers amplified a band of ~330 base pairs corresponding to diphtheria toxin fragment A sequences.
Figure 3B:
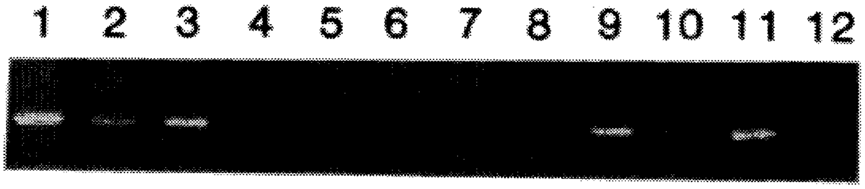
Figure 4:
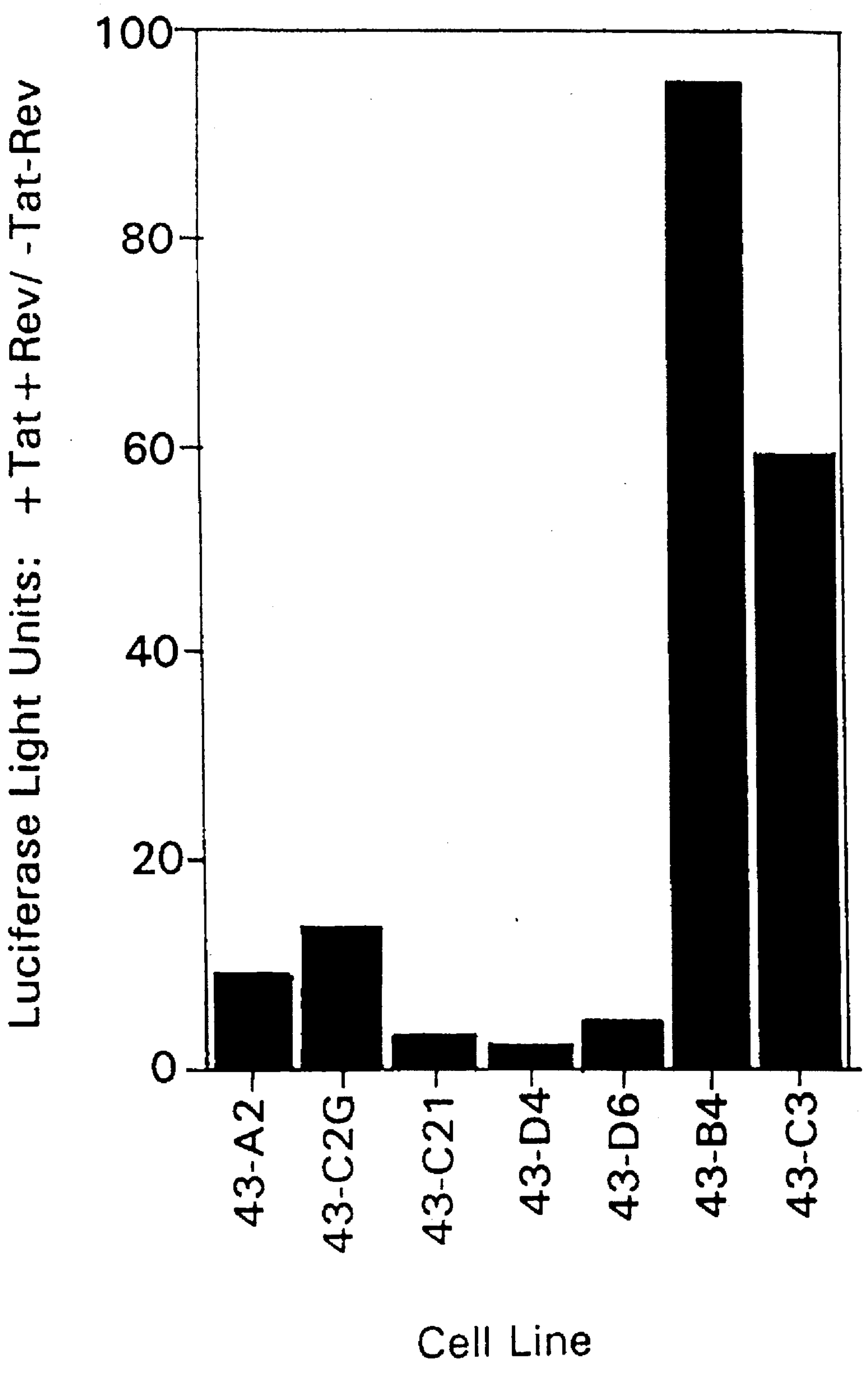
FIG. 4 shows the ratios of induced (electroporated with pLUC43+pH3tat+pH3art) to uninduced light production in five cell lines stably transformed with pTHA43 (43-A2, 43-C2G, 43-C21, 43-D4, 43-D6) and in G418-resistant cell lines lacking the diphtheria toxin fragment A coding sequence of pTH43-B4, 43-C3).

Basal Expression of HIV-regulated DT-A Constructs in Various Cell Types is Significantly Reduced by CRS Sequences in the 3' Untranslated Region Plasmids analogous to pLUCA41 and pLUCA43 were constructed with the coding sequence of the A chain of diphtheria toxin as the HIV-regulated gene instead of luc (FIG. 1). Diphtheria toxin fragment A gene expression from these plasmids, pTHA41 and pTHA43, was assayed indirectly by its inhibition (presumably at the translational level) of luciferase expression from a co-transfected luc reporter plasmid (pRSVL). Luciferase expression and toxin expression should therefore be inversely related. FIG. 3, Panel A, compares basal expression from plasmids pTHA41 and pTHA43 (the latter contains the negative regulatory HIV crs sequences). The results are expressed as a percentage of the control luciferase activity seen when the luc reporter was transfected into parallel samples of cells in the presence of filler DNA only (THA42 as a filler for pTHA41, and pTHA44 as a filler for pTHA43). Basal expression from pTHA43 was substantially reduced compared to that from pTHA41 for all cell types examined. In murine EL-4 T cells, essentially zero basal expression was observed from pTHA43 (FIG. 3, Panel A); and even when the amount of pTHA43 included in the electroporation was doubled to 0.4 μg.

FIG. 2, Panel B, shows trans-activation of pTHA43 in HeLa cells using pRSVL as the co-transfected reporter plasmid. In each case, the numbers are expressed as a percentage of pRSVL co-transfected with pTHA44 (as a filler for pTHA43) and also with pH3tat and/or pH3art when included in the corresponding pTHA43-containing samples. As in FIG. 2, Panel A, basal expression from pTHA43 in the absence of trans-activation resulted in a slightly decreased level of luciferase expression (78% compared to the pRSVL+pTHA44 control, FIG. 2, Panel B). In the presence of both pH3tat and pH3art, diphtheria toxin fragment A gene expression was increased, resulting in a reduction of luciferase activity to 30% of the control. Similar results were obtained for Jurkat and EL-4 cells. The difference between toxin gene expression with pTHA43 alone (in the presence of filler pTHA42) to pTHA43+pH3tat+pH3art, was significant at the $p<0.001$ level (t test for independent samples). In contrast, the addition of either pH3tat or pH3art alone did not significantly trans-activate toxin expression from pTHA43 ($p \geqq 0.20$).

While these data indicated significant trans-activation of diphtheria toxin fragment A gene expression from pTHA43 by Tat+Rev, the effect was not as dramatic as that seen for luciferase expression from pLUCA43 (FIG. 2). Such a comparison is not straightforward because the assay for toxin expression is indirect, and the sensitivity is greater for luciferase. Nevertheless, these results suggest that the HIV-regulated gene itself may influence both the basal expression (lower for pLUCA43 than pTHA43) and the level of trans-activation (higher for pLUCA43 than pTHA43). Chloramphenicol acetyl transferase (CAT) has been used as an HIV-regulated reporter (Rosen et al. (1988) supra), with nearly undetectable basal expression and >800-fold trans-activation (not shown). This supports the notion that the particular HIV-regulated reporter gene being studied can affect HIV-regulated expression by as yet undefined mechanisms.

We attempted to increase the sensitivity of detecting diphtheria toxin fragment A sequence expression from plasmid pTHA43 by using different co-transfected luc reporters. In the dose-response curve shown in FIG. 2, pTHA43+pH3tat+pH3art appeared markedly more inhibitory when pLUCA43 rather than pRSVL (FIG. 2, Panel B) was used as a reporter. For comparison, 0.2 μg of pTHA43 resulted in 95% inhibition of luciferase expression from pLUCA43 but only 70% inhibition of luciferase expression from pRSVL. We have also observed greater inhibition by pTHA43 with pLUCA41 as a reporter compared to pRSVL. These results suggest that the use of pRSVL as a reporter in the transient co-transfection assay (FIG. 3) can lead to underestimation of toxin expression.

HeLa cells were transfected with pSV2-327neo, and either the HIV-regulated diphtheria toxin fragment A plasmid (pTHA43) or the toxin frameshift mutant plasmid (pTHA44). G418-resistant cells were analyzed, as either pooled populations or expanded clones, for luciferase expression from a reporter plasmid, transfected with or without pH3tat+pH3art. The induction of diphtheria toxin fragment A expression from an integrated pTHA43 construct by Tat+Rev should result in lower trans-activated luciferase levels compared to controls. pLUCA43, and HIV-regulated luciferase construct (2), was used as a reporter since we have previously shown that luciferase expression from this plasmid is extremely sensitive to toxin expression. In the pTHA43 pooled population, luciferase expression in the presence of pH3tat and pH3art (expression plasmids for Tat and Rev, respectively) was only about 60% of that obtained with either the pTHA44 pooled population or with parental HeLa cells. Basal expression from pLUCA43 (in the absence of pH3tat and pH3art) was similar in the cells tested, indicating that impaired ability to express transfected DNA did not account for the observed difference in trans-activated expression. This suggested that a substantial fraction of cells in the pTHA43 pool had integrated the regulated diphtheria toxin fragment A gene which could be induced by Tat Rev. As similar numbers of colonies were obtained for the pTHA43 and pTHA44 pools, substantial basal expression of the integrated toxin construct was not apparent.

Using the same assay as for the pooled populations, five separate clones were identified which showed a much larger reduction in trans-activated luciferase expression, to 3–14% of that observed with control G418-resistant clones lacking the diphtheria toxin fragment A coding sequence. These data are shown in FIG. 1. While basal expression levels varied among the positive clones, the amount was insufficient to account for the substantially larger differences in trans-activated expression levels.

If the decreased luciferase expression resulted from activation of diphtheria toxin fragment A gene expression in these clones, then higher luciferase levels should be restored upon inhibition of toxin activity. Diphtheria antitoxin, which was known to inhibit toxin activity, was therefore added to the cell suspension just prior to electroporation with pLUCA43+pH3tat+pH3art. The electroporation conditions used allowed uptake of both DNA and proteins from the medium. The four clones tested showed significant restoration of luciferase expression, with a 2.3 to 6-fold increase compared to the absence of antitoxin. Conversely, HeLa cells and one of the negative clones showed no significant change in luciferase expression upon addition of the antitoxin. This effect was specific for antitoxin, as an "irrelevant" control antiserum (against *H. influenzae*) gave no rescue of luciferase expression.

Example 6

Detection of DT-A Sequences in pTHA43-transformed Cell Lines

PCR analysis was used to demonstrate the presence of diphtheria toxin fragment A coding sequences in the five pTHA43 stable cell lines. Oligonucleotide primers hybridizing to fragment A and HIV LTR sequences were chosen so as to amplify bands of ~330 base pairs (containing diphtheria toxin fragment A sequences) and ~600 base pairs (containing HIV LTR and diphtheria toxin fragment A sequences).

PCR was performed on DNA and reverse-transcribed RNA isolated from the five putative pTHA43-positive clones selected as described above, and also from several pTHA43-negative, G418-resistant, clones. For DNA-based PCR, 6×10$^6$ cells were washed in PBS and lysed in 50 mM Tris-HCL (pH 8), 50 mM EDTA (pH 8), 0.5% SDS and 500 μg/ml Proteinase K (Boehringer Mannheim). Cell lysates were kept at 55° C. overnight and then stored at 4° C. PCR was performed with about 60 ng of DNA from the cell lysate in: 50 mM KC1, 10 mM Tris-HC1 (pH 8.3), 1.5 mM $MgCl_2$, 0.01% gelatin, 0.33 mM dNTPs, 0.04 units/μl of either Taq (Perkin Elmer/Cetus) or VENT (New England Biolabs) polymerases, and 1.67 μM of each primer. Oligonucleotide primers, hybridizing to sequences contained within the first 400 base pairs of diphtheria toxin fragment A sequences, were selected to amplify a band of ~330 base pairs. In some cases an additional oligonucleotide primer was included which hybridized to sequences −165 to −145 of the HIV LTR; this resulted in amplification of a band of −600 base pairs, containing LTR and fragment A sequences. PCR conditions in either the Perkin Elmer/Cetus Thermal Cycler or the BioTherm oven were: 94° C., 1.5 minutes; 50° C., 2 minutes; 72° C., 1.5 minutes, for 30 cycles. PCR products were detected with ethidium bromide staining following electrophoresis in a 3% NuSieve GTG (FMC BioProducts Division, Rockland, Me.), 1% agarose gel.

For RNA-based PCR, total cellular RNA was isolated from cells using standard procedures (Maniatis et al. (1982) *Molecular Cloning:. A Laboratory Manual*, Cold Spring Harbor Laboratory, Cold Spring Harbor, N.Y.). 2.5 μg of RNA was reverse transcribed in PCR buffer containing 1 mM dithiothreitol, 0.2 mM dNTPs, 0.5–1.0 units/μl Rnasin (Promega, Madison, Wis.), 5×10$^5$ units/μl oligo dT12–18 primer (Pharmacia, Piscataway, N.J.), and 100 units/μg Moloney murine leukemia virus reverse transcriptase (BRL). Reverse transcription was performed at 37° C. for two hours; ⅕ of the cDNA was then used for the PCR reaction as described above.

The data with the oligonucleotide primers amplifying the 300 base pair band are shown in FIG. 2, Panel A; all five clones showing decreased pLUCA43 activation, above, were positive for diphtheria toxin fragment A coding DNA sequences while ⅔ G418-resistant clones showing normal pLUCA43 activation were negative for diphtheria toxin sequences. Similar results were obtained using the primers amplifying the 600 base pair band (not shown).

PCR was performed on cDNA, reverse transcribed from total RNA of the five pTHA43 stable clones, isolated with or without prior transfection with pH3tat+pH3art. Additionally, two pTHA43-negative, G418-resistant clones were analyzed. All positive clones showed a diphtheria toxin fragment A sequence band, by ethidium staining, in the presence or absence of pH3tat+pH3art, but no band was observed in the absence of reverse transcription. The negative control samples showed no toxin sequence band under any conditions. Data are shown in FIG. 2, Panel B, for two positive (43- C21 and -D4) and one negative (43-C 3) clones. Thus, diphtheria toxin fragment A gene expression could be detected in the positive clones (but not in the negative clones) in the presence or absence of trans-activation. This is conceivably due to the extreme sensitivity of PCR, and may indicate that the conditions used were not quantitative. Thus, if there was only a very low amount of diphtheria toxin fragment A expression in some of the cells, the band generated may be of equal intensity to that seen if all cells were expressing at a high level.

Example 7 p24 and Luciferase Assays in HeLa Stable Cell Lines Upon Transfection of an HIV Proviral Clone The five HeLa stable clones (43-A2, -C21, -C2G, -D2 and -D4) were transfected with the HIV provirus, HXBΔBgl. HXBΔBgl encodes the HIV genome with a 500 base pair deletion in the env region; thus, viral particles are produced during one round of replication but are noninfectious due to the absence of the envelope protein. p24 levels resulting from the single round of HIV replication were assayed in the HeLa pTHA43 stable clones, and values were compared to those obtained with either parental HeLa cells, or the pooled population transfected with the toxin frameshift plasmid, pTHA44. The data are shown in Table 1, with absorbance readings normalized to 40 μl of cell supernatant.

TABLE 1

Trans-Activation of Luciferase Expression in HeLa Cells Stably Transformed with pLUCA43

| | LUs per 100 μg protein | | Trans-Activation Level* | |
|---|---|---|---|---|
| Plasmid DNA | HeLa luc19 | Pool | HeLa luc19 | Pool |
| pTHA42 (filler) | 26 | 1,009 | 1 | 1 |
| pH3tat + pTHA42 | 573 | 5,511 | 22 | 5.5 |
| pH3art + pTHA42 | 32 | 2,475 | 1.2 | 2.5 |
| pH3tat + pH3art | 2982 | 34,559 | 115 | 34.3 |

*LUs expressed relative to basal expression (pTHA42 alone).

Cells were electroporated with a total of 5.0 μg DNA (consisting of either 5.0 μg of filler pTHA42; 2.5 μg of pH3tat or pH3art with 2.5 μg pTHA42; or 2.5 μg each pH3tat and pH3art), and were harvested 11–14 hours following electroporation. Each number is an average of duplicate samples from one expeiment. "Pool" refers to a pooled population of transformants derived from approximately 600 individual G418 resistant colonies. HeLa luc19 is a cloned transformant.

All five stable cell lines exhibited substantially lower p24 values than either normal HeLa cells or the pTHA44 pool. Three clones exhibited very low p24 values on both days 1 and 2 (between 3.5–17% of control; clones 43-C21, -D4, and -C2G). The other clones (43-D6 and -A2) had somewhat higher p24 values (although still <50% of control), which also increased between days 1 and 2. The higher p24 values in these clones could be due to the higher amount of provirus transfected into these cells (5 μg vs. 2 μg), which could have resulted in more viral production before the full induction of the toxin sequences compared to the other three clones which exhibited a much more dramatic inhibition of p24.

We also examined the ability of the provirus, HXBΔBgl, to trans-activate luciferase expression from co-transfected pLUCA43. Data are presented in Table 2 for two stable cell lines and parental HeLa cells; basal luciferase expression from pLUCA43 was compared to trans-activated luciferase expression with either HXBΔBgl or pH3tat+pH3art.

TABLE 2 p24 levels (absorbance reading) in culture supernatants from pTHA43 stably transformed clones or from HeLa parental cells following transfection with HIV proviral DNA

| Clone | Day 1 (%) | Day 2 (%) |
|---|---|---|
| Experiment 1: | | |
| 43-C21 | .07(3.5) | .23(4.2) |
| 43-D4 | .09(4.9) | .23(4.2) |
| HeLa | 1.88 | 5.46 |
| Experiment 2: | | |
| 43-D6 | .47 (29) | .59 (50) |
| 43-A2 | .38 (23) | .57 (49) |

TABLE 2-continued p24 levels (absorbance reading) in culture supernatants from pTHA43 stably transformed clones or from HeLa parental cells following transfection with HIV proviral DNA

| Clone | Day 1 (%) | Day 2 (%) |
|---|---|---|
| 43-C2G | .17(10) | .20(17) |
| HeLa-pTHA44 pool | 1.64 | 1.17 |

Numbers in parenthesis represent percentages of the corresponding control values obtained with either HeLa cells untransfected (Expt 1) or with a stable HeLa pool transfected with the frameshift diphtheria toxin fragment A plasmid pTHA44 (Expt 2). Values shown were obtained following transfection of either 2 μg (Expt 1) or 5 μg (Expt 2) of the HIV provirus.

Trans-activation of luciferase expression (by either HXBΔBgl or pH3tat+pH3art) was very low in the stable clones compared to HeLa cells, and was even undetectable by day 2 in the clone 43-D4. In HeLa cells, the trans-activated luciferase level was several-fold higher with the provirus than with pH3tat+pH3art on day 1; by day 2, however, the trans-activated levels were similar. Both stable cell lines showed a decrease in trans-activated luciferase levels between days 1 and 2, suggesting that expression of the integrated toxin gene was efficiently induced by both pH3tat+pH3art and the HIV provirus.

p24 assays were performed using an HIV p24 Ag Assay kit (Coulter Immunology) as instructed. 5 to 60 μl of cell supernatant was assayed 24 and 48 hours following transfection of HXBΔBgl. Absorbance was determined using an ELISA microtiter plate reader. As it was determined that the linear range of the assay extended to an absorbance of ~0.7, the color reaction was usually stopped sooner than the 30 minutes indicated in the p24 kit instructions.

Example 8

Construction of a HIV-Regulated DT-A Recombinant Retrovirus

An improved N2-based retrovirus vector LNSX has been described by Miller and Rosman (1989) BioTechniques 7:980; Armentano et al. (1987) J. Virol. 61:1647.

Figure 5A:
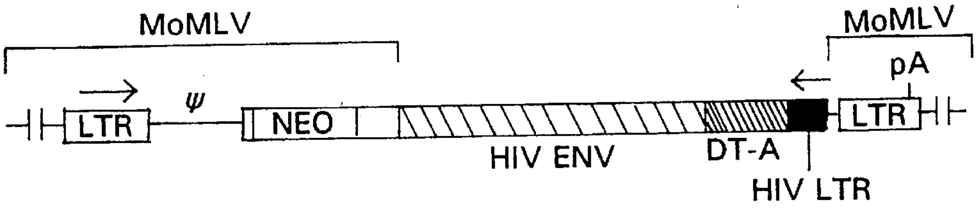
FIG. 5 illustrates the recombinant retroviruses LNX-TH43R and LNX-43R176, which contain HIV-regulated chimeric toxin genes with wild-type and attenuated activities, respectively. NEO represents the neomycin resistance gene, which confers resistance to G418 in cells containing it. The MoLV portions are derived from Moloney Leukemia Virus.
Figure 5B:
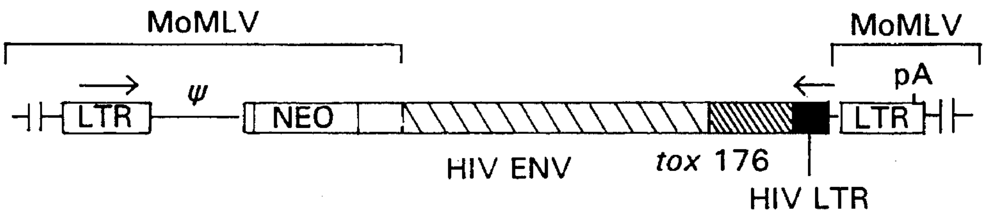

The modifications in LNSX include mutation of the gag start codon and replacement of the upstream region of the vector with the homologous region from Moloney murine sarcoma virus which does not make glycosylated gag. Further modifications include insertion of a unique cloning array downstream to an SV40 early promoter region. This construct eliminates the risk of homologous recombination with endogenous sequences which could generate helper virus, and also yields higher titer viral stocks than previous constructs. LNSX retains the neo gene, so selection for clones which have integrated the retrovirus can be performed in G418. The recombinant diphtheria toxin fragment A-containing proviruses designated LNX-TH43R and LNX-TH43R176 (corresponding to wild type and attenuated toxin activities) were based on LNSX and are diagrammed in FIG. 5.

A XhoI linker was inserted in place of the SV40 promoter of LNSX. A XhoI fragment from pTHA43, containing the HIV LTR from −167 to +80, the diphtheria toxin fragment A sequence encoding a protein of wild-type activity, and 5925–7325 of the env region of HIV (containing CRS and RRE sequences) was then inserted into the XhoI site of the modified LNXX. Restriction digests were used to identify both orientations of the insert. LNX-TH43, which has the same orientation as the viral promoter, should utilize the polyadenylation signal in the retroviral 3' LTR. LNX-Th43R, where the HIV-regulated diphtheria toxin fragment A (wild-type activity) coding sequence is in the orientation opposite to that retrovirus LTR, was not specifically provided with a polyadenylation signal for the toxin transcript. In pLNX-TH- 43R, the toxin sequences are transcribed from the HIV-1 promoter in the opposite orientation to the neo gene from the MLV LTR. pLNX-TH43R176 was generated by inserting a NcoI-SalI fragment that contains the tox176 attenuated fragment A coding sequence into pLNX-TH43R which was digested with NcoI (partial) and SalI. pLNX-TH43R176 is identical to pLNX-TH43R except for the tox176 mutation.

LNX-TH43 and LNX-TH43R were tested in transient assays. The wild-type activity retroviral constructs were electroporated into cells along with a luciferase reporter gene (pLUCA43) and pH3tat+pH3art. Expression of toxin activity from the retroviral constructs, as measured by inhibition of luciferase expression, was similar to that of the plasmid pTHA43. This data is summarized below for two different amounts of the indicated construct:

| | % control LUC expression with: | | |
|---|---|---|---|
| μg DT-A construct | pTHA43 | LNX-TH43 | LNX-TH43R |
| 0.05 | 6 | 23 | 13 |
| 0.2 | 3.6 | 7.1 | 4.9 |

These results show that Tat+Rev dependent expression of the regulated toxin gene was maintained after insertion into the provirus (in either orientation) at a level comparable with that from the parental plasmid, pTHA43. To date, it has not been possible to package recombinant retroviruses in which the orientation of the chimeric diphtheria toxin fragment A gene is in line with the retrovirus LTR. This may be due to the internal HIV LTR providing a polyadenylation which results in premature termination of viral transcripts.

LNX-TH61R contains the HIV-IIIb LTR sequences (−453 to +80), the NF-kB mutant promoter, the wild-type-like diphtheria toxin fragment A and a monomeric TAR sequence. LNX-TH61R176 is the same except that the tox176 is substituted for the wild-type fragment A coding sequence. LNX-TH91R and LNX-TH91R176 contain the HIV LTR, the wild-type NF-kB region and a dimer of the TAR sequence and the wild-type and attenuated tox176 diphtheria toxin fragment A coding sequences, respectively. LNX-TH93R176 contains the tox176 coding sequence under the regulatory control of the HIV NIT-E LTR, wild-type NF-kB region and monomeric TAR sequence. LNX-TH95R176 contains the tox176 coding sequence under the regulatory control of the HIV JR-CSF LTR, wild-type NF-kB region and monomeric TAR sequence. LNX-TH93R176 contains the tox176 coding sequence under the regulatory control of the HIV JR-FL LTR, wild-type NF-kB region and monomeric TAR sequence. The NIT-E is a clinical HIV variant which is characterized as having low basal levels of expression from the LTR but good trans-activation levels (Kohno and Uchida (1987) J. Biol. Chem. 262: 12298). JR-CSF and JR-FL are two clinical isolates from the same patient; JR-CSF is T-cell tropic while JR-FL replicates in macrophage cells. This tropism was shown to be determined by a 157 amino acid region in the gp120 protein of JR-FL (O'Brien et al. (1990) Nature 348:69).

Intermediate plasmids LNX-TH43R (or pLNX-43R176)-ΔX1 and Δ2 are generated by partially digesting pLNX- TH43R (or -TH43R176) with XhoI, gel purifying the linear form, filling in with Klenow polymerase and religating. ΔX1 is filled in at the XhoI site 3' to env while ΔX2 is filled in at the XhoI site 5' to the HIV LTR; these are distinguished the restriction digest patterns displayed by agarose gel electrophoresis after by digestion with ClaI and XhoI. pLNX-TH43R (or -TH43R176)-ΔX1 are digested with XhoI, blunt-ended with Klenow DNA polymerase and then partially digested with NcoI. The 9 kb NcoI fragment (minus the HIV LTR sequences from −167 to +80) is gel purified and phosphatased. An AvaI-NcoI fragment from pTHA61 (containing −154 to +80 and including the NF-kB binding site mutations) is isolated after first blunting the AvaI end with Klenow; this fragment migrates apart from the approximately 375 bp NcoI-AvaI fragment containing the toxin fragment A coding sequence. The insert from pTHA61 is directionally inserted into LNX-TH43R (or -43R176)-Δas a blunt end/sticky end ligation, generating pLNX-TH61R (or pLNX-TH- 61R176).

To generate LNX-TH91R and pLNX-TH91R176, a XhoI-HindIII fragment containing −167 to +80 of the HIV LTR is isolated from plasmid IIIex7 (C. Rosen), blunt-ended with Klenow DNA polymerase and inserted into LNX-TH43R (or -TH43R176)-ΔX1 filled in at both XhoI sites as described above. Proper orientation is confirmed by restriction analysis.

Similar methods are used to prepare the plasmids containing the control sequences from the HIV NIT-E, JR-CSF and JR-FL strains.

Example 9

Packaging of DT-A Recombinant Retroviruses

Packaging cell lines PE501 and PA317 produce ecotropic (infecting rodent cells) and amphotropic (capable of infecting both rodent and a human cells) retroviruses. These cell lines are derived from mouse NIH 3T3 cells, and they have mutations in the helper function sequences (deletion of the packaging signal and the LTRs) which minimize the risk of homologous recombination between retroviral and endogenous sequences. However, rare recombination events have been observed with certain retroviral vectors, but not with G1-based vectors.

Alternative packaging cell lines include GP+envAM12 (amphotropic) and GP+E-86 (ecotropic; Markowitz et al. (1988) Virology 167:400–406; Markowitz et al. J. Virol. 62:1120–1124). These cell lines were constructed by introducing helper functions gag and pol on one plasmid and env on a second plasmid. The cloned helper functions do not contain packaging signal sequences or the 3' LTR sequences. Three independent recombination events would be required to generate helper virus.

HIV-regulated diphtheria toxin fragment A sequence-containing retrovirus were packaged at about $10^3$ *to* $10^4$ CFUs/ml. In the absence of high titers required to approach an efficiency of 100%, all the experiments described were performed following growth in medium containing G418 to select for cells transduced with the recombinant retrovirus.

Two protocols were compared for the production of amphotropic retrovirus. The packaging cell lines tested were Psi2 (Mann et al. (1983) Cell 33:153–159), PA317 and PE501 cells (Miller and Rosman (1989) BioTechniques 7:980–984; Miller and Buttimore (1986) Mol. Cell. Biol. 6:2895–2902).

In a first protocol, LNXX or LNXX-TH43R176 was transfected by electroporation into PA317 cells (5 μg DNA per $2\times10^6$ cells in 100 μl volume; Gene Pulser setting at 280 volts, 250 μfarad). After 48 hours, cell-free supernatant was harvested and used to infect PE501 cells in the presence of Polybrene (4 μg/ml). G418 was incorporated into the culture medium at a concentration of 750 μg/ml). G418-resistant cells were cloned using sterile cotton swabs wet with trypsin solution for transfer to multiwell plates. PE501 clones were screened for diphtheria toxin fragment A coding DNA and mRNA sequences in the virus-containing supernatant using PCR technology as described by Morgan et al. (1990) Human Gene Ther. 1:135–149.

Four clones of PE501 cells (2B, 3A, 4B, 5B) positive for toxin DNA and HIV LTR sequences and one PCR-negative clone (1C) derived from transfection with LNXX were used in a co-cultivation "ping-pong" procedure (Bestwick et al. (1988) Proc. Natl. Acad. Sci. USA 85:5404–5408) with PA317 cells to produce amphotropic virus. Aliquots of transduced H9 cells were selected in G418-containing medium, and they were either maintained as pooled populations or were cloned by limiting dilutions in microtiter multiwell plates.

In a second protocol, aliquots of Psi2 cells were transfected with LNXX, LNX-TH43R and LNX-TH43R176 as described above for PA317 cells. After 48 hours supernatants were collected and used to infect PA317 cells in the presence of Polybrene. Psi2 cells were used in place of PE501 cells because no G418-resistant were obtained when the supernatants were harvested from transfected PE501 cells. Virus-containing supernatant from PCR-positive PA317 clones were used to infect H9 cells, and transduced H9 cells were selected with G418 and maintained as described above.

The percentages of G418-resistant cell clones which scored positive for toxin sequences were similar for the two protocols for LNX-43R176. For the first protocol, 11/22 clones were positive for HIV and toxin sequences; of these 10 were also positive for the RNA sequences as well. In the second protocol, both LNX-TH43R and LNX-43R176 were used. 6/10 clones transduced with LNX-TH43R176 were positive for DNA sequences and of these, 5/6 were also positive for RNA sequences. By contrast, a lower percentage of positive clones were found for LNX-TH43R. Only 2/8 clones transfected with LNX-TH43R were positive for the relevant DNA sequences, and one of these was also positive for the corresponding RNA sequences. Without wishing to be bound by any theory, this may have been due to internal HIV LTR sequences interfering with full length viral RNA production or due to the presence of cryptic splice sites.

The G1 vector backbone (developed by Genetic Therapy, Inc.) (Gaithersburg, Md.) has been approved for use in human clinical experiments. G1 is based on the vector N2 (Armentano et al. (1987) J. Virol. 61:1647–1650), but about 100 bp of DNA have been eliminated. Those deleted sequences would have permitted homologous recombination between the retroviral vector and constitutively expressed sequences in the packaging cells and subsequent generation of helper virus. In addition to the MoLV LTRs, the G1 backbone contains a packaging signal, sequences derived from MoLV gag (with a modification in the start codon) and multicloning sites into which a gene with an internal promoter and other regulatory sequences can be inserted. The HIV-regulated diphtheria toxin fragment A chimeric sequences are introduced from appropriate intermediate plasmids, in both orientations, with testing for packaging of HIV-regulated toxin construct virus in each orientation after introduction into desired potential packaging cell lines.

One of ordinary skill in the art can manipulate the G1 vectors to incorporate the HIV-regulated diphtheria toxin fragment A coding sequences of the present invention without the expense of undue experimentation. HIV-regulated toxin genes contemplated include those from LNX-TH43R, LNX-TH61R, LNX-TH91R, LNX-TH93R, LNX-TH43R176, LNX-TH61R176, LNX-TH91R176, LNX-TH93R176 and the like.

These packaging cell lines into which the HIV-regulated toxin retroviral constructs are introduced and tested for production of helper virus. One assay for helper virus production is the Sarcoma$^+$Leukemia$^-$(S+L–) assay. Murine, mink and feline cells lines have been developed as indicators of replication-competent helper virus (Peebles et al. (1971) J. Virol. 8:690–694; Ishimoto et al. (1980) J. Virol. 36:128–212; Lee et al. (1972) J. Natl. Cancer Inst. 49:55–59; Belmont et al. (1988) Mol. Cell. Biol. 8:5116–5125; Scarpa et al. (1991) Virology 180:849–852). The basis for the S+L–assay is that some cell lines infected with sarcoma viruses appear morphologically normal unless superinfected with leukemia virus, in which case the morphology changes to that of the transformed (leukemic) phenotype. The presence of helper virus (derived from MolV stocks in the murine packaging cells) can thus be detected by conversion of the normally flat indicator cells to transformed foci. The S+L–assay is performed in the presence of conditioned medium from the producing packaging cell line; the lack of transformed focus formation indicates the absence of helper virus. One can also assay the culture supernatant from 3T3 cells passaged for several rounds following infection with the test recombinant retroviral stock. The phenotypic conversion, when the leukemia virus is present, takes from about 5 days to several weeks.

A second assay for helper virus is the marker rescue assay. In this assay one determines whether replication-competent virus can be recovered following infection of non-producing cells, e.g., NIH 3T3 cells (Belmont et al. (1988) supra). NIH 3T3 cells are infected with test culture supernatant and the transduced cell fraction is selected with G418. Pooled populations of selected cells are passaged for several weeks, after which time their supernatants are placed on fresh NIH 3T3 cells followed by G418 selection. If there are no neo-transducing virus in the supernatant of the G418-resistant 3T3 pool, assurance is provided that no helper virus was generated. The marker rescue assay takes about 4 weeks to complete.

A third assay for helper virus production is a PCR assay, as described by Scarpa et al. (1991) supra. Either RNA-based or DNA-based PCR can be used to detect the presence of replication-competent virus. Sequences used as PCR primers must not be present in the recombinant retrovirus or a false positive results. PCR primer sequences can be derived from the pol and env genes (Scarpa et al. (1991) supra). NIH 3T3 cells are infected and selected in G418 as described for the marker rescue assay, and then the helper-specific PCR is run on the culture supernatant of the pooled cells. RNA-based PCR has the potential advantage that it is less likely to detect "residual" sequences remaining from the initial infection than DNA-based PCR.

There have been indications that G418 does not afford the best selection for retrovirally transduced PBMCs. Alternative selective markers, well known and available to the art, including but not limited to histidinol, methotrexate and hygromycin resistance genes, can be substituted for the neo marker.

Example 10

Inhibition of HIV Production in Transduced Cell Lines

Diphtheria toxin fragment-A transduced H9 cells were selected and several clonal isolates were obtained. Resultant cell lines R9-D1 and B4 contained HIV-regulated fragment A seuqences (from LNX-TH43) and cell lines 3A5-A11 and 5B10-C8 contained the HIV-regulated tox176 sequence. The effects of HIV-IIIb challenge on these four cell lines were compared with an untransduced H9 control.

Cells were incubated with 500 to 5000 $TCID_{50}$ of HIV-IIIb, and supernatants were sampled periodically for HIV p24 measurement using a commercially available kit (Coulter). The quantity of p24 is an indication of HIV replication and its extent.

R9-D1 and 3A5-A11 exhibited complete inhibition of HIV production over a 6 day period, while the R9-B4 and 5B10-C8 showed measurable, though lower than control, HIV production within a few days of HIV-IIIb infection. By 8–11 days after infection, p24 production was similar to the controls from all clones except R9-D1. By contrast, R9-D1 cells were completely inhibited for p24 production even at day 31, and was also negative for infective HIV sequences on day 59.

Receptor (CD34) loss as a mechanism for the apparent resistance to HIV infection and replication was ruled out in two ways. Fluorescence-activated cell sorting (FACS) using antibody specific for CD34 (Dako Corp., Carpinteria, Calif.) showed that the percentage of cells staining positive for CD34 in the R9-D1 cell line (80%) was similar to that observed for the H9 control cell population (88%). In contrast for R9-C4, which was markedly restrictive for HIV production as measured by p24 expression, expression of CD34 on the cell surface was significantly reduced (25%) as compared to control H9 cells (88%). Nonetheless, it is noted that R9-D1 cells were capable of being infected by the clinical HIV isolate A018a but not HIV-IIIb. It is understood that HIV cis-acting regulatory sequences from other HIV strains, e.g., from clinical isolates, may be substituted for those exemplified herein.

Representative HIV-regulated toxin transduced H9 cell lines were challenged with the clinical isolate HIV A018a (obtained from Dr. D. Richman) or were transfected by electroporation with molecular clones of HIV called pYU-2 and pSG.1 (from Drs. B. Ghosh and B. Hahn). The clinical isolates exhibited different phenotypes and tissue tropisms (Li et al. (1991) J. Virol. 65:3973–3990). All transduced clones tested were protected for at least 31 days from infection by A018a if the virus was washed out after 2 hours of infection. Protection was not conferred if the virus-containing medium was not removed from the cell culture. Similar results were obtained with other HIV-regulated toxin gene-containing H9 cell lines. Without wishing to be bound by any particular theory, it is postulated that there may be a breakdown of protection at high cellular virus loads and that washing out unabsorbed virus at two hours prevents the high virus load effect.

Electroporated molecular clones generated high levels of p24 in control H9 cell populations whereas p24 expression was undetectable in R9-D1, even up to 53 days post infection, as shown in Table 3.

TABLE 3

| pg p24 per 200 μl of culture supernatant from cells electroporated with pHXB2D(=HIV IIIB) | | | | | | |
|---|---|---|---|---|---|---|
| | | | PYU-2 | | pSG3.1 | |
| Day | H9 control | R9-D1 | H9 control | R9-D1 | H9 control | R9-D1 |
| 11 | 191 | 0 | 189 | 0 | 193 | 0 |
| 26 | 284 | 0 | 258 | 0 | 283 | 0 |
| 53 | N.D. | 0 | N.D. | 0 | N.D. | 0 |

(N.D. = not determined)

Example 11

Transduction of HIV-regulated DT-A sequences into PBMCs and CD34+ BM cells.

Retroviral transduction of human peripheral blood monocytic cells (PBMCs) and bone marrow (BM) cells has been described (See, e.g., Culver et al. (1991) Human Gene Ther. 2:107–109; Miller (1992) Cur. Topics in Microbiol. Immunol. 158:L1–24; Culver et al. (1991) Proc. Natl. Acad. Sci. USA 88:3155–3159; Smith (1992) J. Hematother.1:155–166; Bregni et al. (1992) Blood 80:1418–1422; and references cited therein). Results by the present inventors support the findings of others that co-cultivation is optimal for transduction. The present inventors found that improved results were obtained when CD34+ cells were selected prior to the co-cultivation for transduction. This increased the percentage of CD34+ cells from 43% to 76%. Following several more days in culture, the percentage increased to >90%. Some studies incorporated a recombinant derivative of the retroviral vector LNPOZ packaged in PA317 cells. Liposome-mediated DNA introduction of recombinant retroviruses (or other recombinant DNA molecules) containing an HIV-regulated toxin coding sequence is an alternative to co-cultivation for genetically engineering BM cells, PBMCs and/or CD34+ cells. LNPOZ is described in Adam et al. (1991) J. Virol. 65:4985–4990 and was provided by Dr. D. Miller. LNPOZ carries the β-galactosidase gene which is useful as a marker.

When LNPOZ was used with PBMCs after 4 days of co-cultivation with retrovirus producer cells, β-galactosidase assayed by staining overnight according to a standard histochemical method (Bondi et al. (1982) Histochemistry 76:253–158) or by FACS analysis with the fluorescent substrate fluorescein di (β-D-galactopyranoside (Sigma Chemical Co., St. Louis, Mo.) (Nolan et al. (1988) Proc. Natl. Acad. Sci. USA 85:2603–2607). FACS is preferred, especially when sorting by CD34 positive reaction is coupled with sorting by the positive fluorescence reaction of β-galactosidase, particularly when cells were transduced by co-cultivation.

Variable results were obtained in transduction of BM cells. It was determined that control BM cells appear to exhibit a higher percentage of β-galactosidase-positive (as high as 10%) than did the PBMCs. The high background makes analysis difficult. Without wishing to be bound by any particular theory, it is suggested that persistence of the packaging cells contributes to the high background and to variability in results. A second theory is that variability and/or background reaction may result from the inherent instability of the β-galactosidase substrate.

To confirm that HIV regulation of expression of diphtheria toxin fragment A sequences conferring wild-type toxin activity and attenuated activity (tox176) is sufficiently tight in human primary cells so as not to result in cell death in the absence of HIV trans-acting factors, transient expression assays are carried out. Conditions for the electroporation stimulated PBMCs have been described (Cann et al. (1988) Bio-Rad Bulletin 1348). Diphtheria toxin activity is measured by its inhibition of a co-transfected HIV-regulated luciferase reporter gene expression. Pilot experiments performed with constitutive luciferase and HIV-regulated luciferase constructs have been successful, and the preliminary results indicate that HIV regulation is sufficiently stringent in the PBMCs for use with the HIV-regulated DT-A and tox176 coding sequences.

One of ordinary skill in the art can manipulate the LNPOZ vectors to incorporate the HIV-regulated diphtheria toxin fragment A coding sequences of the present invention without the expense of undue experimentation. HIV-regulated toxin genes contemplated include those from LNX-TH43R, LNX-TH61R, LNX-TH91R, LNX-TH93R, LNX-TH43R176, LNX-TH61R176, LNX-TH91R176, LNX-TH93R176 and the like. The recombinant LNPOZ vectors are called LNPOZ-TH 43R, LNPOZ-TH43R176, LNPOZ-TH61R, LNPOZ-TH61R176, LNPOZ-TH91R, LNPOZ-TH91R176, LNPOZ-TH93R and LNPOZ-TH93R176 and so on.

Example 12

Assay for Effectiveness of HIV-Regulated Viral Vectors

Viral vectors carrying HIV-regulated diphtheria toxin fragment A coding sequences are tested for their ability to confer resistance to HIV-1 in PBMCs, BM cells and in the reconstituted SCID mouse system.

The cells are transduced with vectors containing the HIV-regulated diphtheria toxin fragment A sequences and then infected with HIV at doses of 5000–500,000 $TCID_{50}$ per $10^6$ cells. HIV production is assayed as follows:

p24—p24 levels are monitored periodically over a period of several months as described in Harrison et al. (1992) AIDS Res. and Human Retroviruses 8:39–45; Harrison et al. (1992) Human Gene Ther. 3461–469.

Syncytia formation—C8166 cells, derived from human umbilical cord blood lymphocytes, form syncytia rapidly (within hours) upon exposure to cells expressing HIV gp120 antigens. Cells are observed through a light microscope following HIV infection. Multinucleate cells having a diameter three times greater than control cells are scored as syncytia. $5\times10^4$ cells into which an HIV-regulated toxin-containing vector had been are introduced are infected with HIV doses as described above. 100 μl of infected cells at $10^5$ per ml are cultured in a 200 μl total volume with $5\times10^3$ C8166 cells in a 96 well flat bottom microtiter plate. HIV production is assayed over a two week period, at three day intervals. Syncytia are counted 4 hours later.

Immunofluorescent assay—Infected cells are assayed for HIV production over a two week period, at three day intervals. HIV infections are performed as above. Polyclonal sera from HIV-positive individuals with high antibody titers as indicated by ELISA are used. Antibodies in the polyclonal sera recognize surface antigens, usually env determinants, although some gag reactivity may be observed. HIV-infected cells, suspended at $1\times10^6$ cells per ml are fixed in methanol. 10 μl of fixed cells are incubated with a 1:1000 dilution of polyclonal HIV antiserum for 30 min, washed with PBS, and then stained with goat anti-human Ig-FITC. Cells are observed microscopically, and cells having greater than 50% circumferential staining are scored positive.

Cells showing longterm resistance to HIV infection are examined for latent HIV infection and/or late breakthrough. Uninfected PBMCs are obtained from HIV-negative donors and suspended at $10^6$ per ml in culture medium containing 1 μg per ml phytohemagglutinin and 20 μg per ml recombinant interleukin-2 to produce PHA blasts. After 72 hours 1 ml of culture supernatant from an HIV-infected, resistant cell population is added to $3\times10^6$ PHA blasts in a 3 ml volume. This culture is maintained for 28 days,with fresh PHA blasts added weekly. After 28 days any clone displaying a p24 value lower than 30 pg per ml in this mixed culture system is considered not infected with HIV.

Quantitative PCR is used to detect residual HIV sequences in cells determined to be HIV-resistant, using the densitometric analysis of digoxigenin-labeled PCR products and the Genius chemiluminescent system (Boehringer Mannheim, Indianapolis, Ind.).

FACS analysis is performed on all cell cultures before and during HIV infection to determine that resistance to HIV is not due to CD4 receptor loss.

CD4+ cells are enriched from PBMC populations using "selection" flasks (Applied Immune Sciences, Inc.) coated with either anti-CD4 or anti-CD8 antibody to collect the adherent or the nonadherent cells, respectively. Retroviral infection of CD4-enriched PHA blasts is accomplished by co-cultivation with producer cells as described herein. Controls comprise the frameshift mutant fragment A coding sequence.

The transduced cells as pools are assayed for both unselected and G418-selected populations. It is unlikely, even with drug selection to isolate a population in which all cells are transfected with the HIV-regulated toxin gene. Thus, in a population of cells, one expects to see only partial inhibition of HIV production. Individual clones of PHA blasts are isolated as described in Harrison et al. (1992) Human Gene Ther. 3:461–469. Briefly, cells are cloned by limiting dilution in microtiter well plates, with the weekly addition of feeder cells. G418 (or other selective agent) is applied to vigorously growing clones. DNA-based PCR is used to confirm the presence of the HIV-regulated toxin sequences in the pooled populations and in the cloned. Only PCR-positives are studied further.

Clones or pooled populations of cells are challenged by HIV infection with laboratory and clinical isolates. HIV production is monitored as above. Cells demonstrating no (or impaired) HIV production over a two month period by the criteria given above are scored resistant to HIV infection. In the pooled populations, HIV resistant cells stably engineered to contain the HIV-regulated diphtheria toxin fragment A sequences have a selective advantage over those cells capable of being infected (and killed) by HIV. Thus, a HIV-resistant population can emerge.

Pluripotent BM hematopoietic stem cells are transfected to contain the HIV-regulated toxin gene, generating immune-competent, HIV-resistant cells which can reconstitute components of the immune system. CD34+ BM cells are known to be capable of being infected by HIV-1 in vitro and are known to differentiate in vivo into the more mature cells which are known targets for HIV infection. Thus, this approach for generating HIV-resistant cells does not depend on the CD34+ cells themselves being infected by HIV. The BM cells are genetically engineered to contain the HIV-regulated toxin genes using the methods described above for the PBMCs.

Two approaches are taken to demonstrate that the HIV-regulated toxin gene mediates HIV resistance in the BM cells and PBMCs. First, an RNA-based PCR is used to demonstrate induction of toxin coding mRNA following HIV infection.1 Second, cells displaying HIV resistance are transfected with diphtheria toxin-resistant mutant EF-2 gene. If HIV resistance is due to the expression of toxin within the cells, then the toxin-resistant EF-2 should at least partly restore the ability to propagate HIV. CD+ FACS before and during the time course following HIV infection indicates if HIV resistance is due to CD4 receptor loss.

Reconstitution of SCID mice with PBMCs or BM cells transfected with the HIV-regulated chimeric toxin sequences and subsequent challenge with HIV are carried out. Some hu-PBL-SCID mice develop AIDS-related symptoms so the reconstitution of the SCID mice with the containing HIV-regulated diphtheria toxin fragment A coding sequences carried by the retroviral vectors described herein are impaired in their ability to be infected by HIV.

We claim:

1. A stably transformed cell line of mammalian origin, wherein the genome of said cell line has been genetically engineered to contain an HIV-regulated chimeric diphtheria toxin gene, wherein said diphtheria toxin gene is expressed under the regulatory control of HIV cis-acting sequences and HIV trans-acting factors, wherein the expression of said HIV-regulated chimeric diphtheria toxin gene is activated by HIV trans-acting factors present when and if said cell line becomes HIV-infected, whereby said HIV-infected cell is selectively killed.

2. The stably transformed cell line of claim 1 wherein said HIV-regulated chimeric toxin gene encodes a diphtheria toxin fragment A having wild-type activity.

3. The stably transformed cell line of claim 1 wherein said toxin gene is tox176.

4. The stably transformed cell line of claim 1 wherein said HIV trans-acting factors comprise an HIV Tat protein and an HIV Rev protein.

5. The stably transformed cell line of claim 1 wherein said HIV cis-acting sequences of said chimeric toxin gene comprise an HIV TAR element, an HIV RRE element and an HIV crs element.

6. The stably transformed cell line of claim 5 wherein said HIV cis-acting sequences in said chimeric toxin gene comprise nucleotides from −167 to +80 of an HIV LTR positioned upstream of said chimeric toxin gene and further comprising nucleotide 5925-8608 of HIV-1 positioned downstream of said toxin coding sequence.

7. The stably transformed cell line of claim 5 wherein said HIV cis-acting sequences in said chimeric toxin gene comprise nucleotides from −167 to +80 of an HIV LTR positioned upstream of said chimeric toxin gene and further comprising nucleotide 5925-8490 of HIV-1 positioned downstream of said toxin coding sequence.

8. The stably transformed cell line of claim 5 genetically engineered by the introduction of one of pTHA43, pTHA43-176, pTHA61, and pTHA61-176.

9. The stably transformed cell line of claim 5 genetically engineered by the introduction of one of LNX-TH43R, LNX-TH43R176, LNX-TH61R, LNX-TH61R176, LNX-TH91R, and LNX-TH91R176.

10. A recombinant DNA molecule suitable for the stable transformation of a cell line of mammalian origin to effect selective killing of a stably transformed cell infectible with HIV, said recombinant DNA molecule comprising a vector portion and a chimeric HIV-regulated diphtheria toxin gene portion, wherein said chimeric diphtheria toxin gene is expressed under the regulatory control of HIV cis-acting regulatory sequences and HIV trans-acting factors, and wherein the expression of said chimeric diphtheria toxin gene is activated by trans-acting factors of HIV, whereby when said cell line is infected with HIV, the HIV trans-acting factors activate the expression of said chimeric diphtheria toxin gene, thus killing the HIV-infected stably transformed cell.

11. The recombinant DNA molecule of claim 10 wherein said toxin gene encodes a diphtheria toxin fragment A having wild-type activity.

12. The recombinant DNA molecule of claim 10 wherein said toxin gene is tox176.

13. The recombinant DNA molecule of claim 10 wherein said HIV trans-acting factors comprises an HIV Tat protein and an HIV Rev protein.

14. The recombinant DNA molecule of claim 10 wherein said cis-acting sequences comprise an HIV Tar element, an HIV RRE element and an HIV-1 crs element.

15. The recombinant DNA molecule of claim 14 wherein said HIV cis-acting sequences comprise nucleotides from −167 to +80 of an HIV LTR positioned upstream of said toxin gene and further comprising nucleotides 5925–8490 of HIV-1 positioned downstream of said toxin coding sequence.

16. The recombinant DNA molecule of claim 14 wherein said HIV cis-acting sequences comprise nucleotides from −167 to +80 of an HIV LTR positioned upstream of said toxin gene and further comprising nucleotides 5925–8608 of HIV-1 positioned downstream of said toxin coding sequence.

17. The recombinant DNA molecule of claim 14 wherein said recombinant DNA molecule is one of pTHA43, pTHA61, pTHA91, pTHA43-176, pTHA61-176 and pTHA91-176.

18. The recombinant DNA molecule of claim 14 which is one of LNX-TH43R, LNX-TH43R176, LNX-TH61R, LNX-TH61R176, LNX-TH 91R, and LNX-TH91R176.

19. The recombinant DNA molecule of claim 14 wherein said vector portion is derived from G1.

20. The recombinant DNA molecule of claim 14 wherein said vector portion is derived from LNPOZ.

* * * * *